United States Patent
Laughlin et al.

(10) Patent No.: US 12,134,782 B2
(45) Date of Patent: Nov. 5, 2024

(54) T CELLS DERIVED FROM UMBILICAL CORD BLOOD

(71) Applicant: Abraham J and Phyllis Katz Cord Blood Foundation, Cleveland, OH (US)

(72) Inventors: Mary Laughlin, Cleveland, OH (US); Jeong Su Do, Cleveland, OH (US)

(73) Assignee: Abraham J and Phyllis Katz Cord Blood Foundation, Cleveland, OH (US)

(*) Notice: Subject to any disclaimer, the term of this patent is extended or adjusted under 35 U.S.C. 154(b) by 912 days.

(21) Appl. No.: 16/479,253

(22) PCT Filed: Jan. 29, 2018

(86) PCT No.: PCT/US2018/015667
§ 371 (c)(1),
(2) Date: Jul. 19, 2019

(87) PCT Pub. No.: WO2018/140850
PCT Pub. Date: Aug. 2, 2018

(65) Prior Publication Data
US 2019/0376032 A1 Dec. 12, 2019

Related U.S. Application Data

(60) Provisional application No. 62/595,243, filed on Dec. 6, 2017, provisional application No. 62/552,119, filed on Aug. 30, 2017, provisional application No. 62/451,364, filed on Jan. 27, 2017.

(51) Int. Cl.
*C12N 5/0783* (2010.01)
*A61K 35/17* (2015.01)

(52) U.S. Cl.
CPC ............ *C12N 5/0637* (2013.01); *A61K 35/17* (2013.01); *C12N 2501/15* (2013.01); *C12N 2501/2302* (2013.01); *C12N 2502/1358* (2013.01)

(58) Field of Classification Search
None
See application file for complete search history.

(56) References Cited

U.S. PATENT DOCUMENTS

| | | | |
|---|---|---|---|
| 6,194,207 B1 * | 2/2001 | Bell | C12N 5/0636 435/377 |
| 2011/0268716 A1 | 11/2011 | Zheng | |
| 2013/0259829 A1 * | 10/2013 | Newell | A61P 35/00 435/7.1 |
| 2020/0263131 A1 * | 8/2020 | Riley | C12N 5/0637 |

FOREIGN PATENT DOCUMENTS

WO WO 2017062035 * 4/2017

OTHER PUBLICATIONS

Hagmann et al., Clinical and Experimental Immunol, 2013,v. 173, pp. 454-462.*
Schmidt et al J of Visualized Experiments, 2016, v. 118 p. 1-10.*
Schmitt et al Frontiers in Immunology, 2013, p. 1-13.*
European extended Search Report for EP Application No. 18744913.7 mailed Dec. 10, 2020 (11 pages).
Fan et al., "Mesenchymal Stromal Cell Supported Umbilical Cord Blood ex vivo Expansion Enhances Regulatory T Cells and Reduces Graft Versus Host Disease," Cytotherapy, 2013, 15:610-619.
Horwitz et al., "Natural and TGF-β-Induced Foxp3+CD4+ CD25+ Regulatory T Cells are not Mirror Immages of Each Other," Trends in Immunology, 2008, 29(9):429-435.
Lu et al., "Characterization of Protective Human CD4+ CD25+ Foxp3+ Regulatory T Cells Generated with IL-2, TGF-β and Retinoic Acid," PLoS One, 2010, 5(12):e15150 (12 pages).
Shi et al., "CD4+ Foxp3+ Regulatory T Cells Induced by TGF-β, IL-2 and All-Trans Retinoic Acid Attenuate Obliterative Bronchiolitis in Rat Trachea Transplantation," International Immunopharmacology, 2013, 11:1887-1894.
Tao et al., "Foxp3, Regulatory T Cell, and Autoimmune Diseases," Inflammation, 2017, 40(1):328-339.
PCT International Search Report and Written Opinion for PCT/US2018/015667 mailed Jul. 20, 2018 (15 pages).
PCT International Preliminary Report on Patentability for PCT/US2018/015667 mailed Feb. 22, 2019 (10 pages).
Chapter II Demand and Reply to Written Opinion submitted on Nov. 27, 2018 (112 pages).
Brunstein et al., "Infusion of ex vivo Expanded T Regulatory Cells in Adults Transplanted with Umbilical Cord Blood: Safety Profile and Detection Kinetics," Blood, 2011, 117(3):1061-1070.
Fransson et al,. "CAR/FoxP3-Engineered T Regulatory Cells Target the CNS and Suppress EAE Upon Intranasal Delivery," Journal of Neuroinflammation, 2012, 12 pages.
Lee et al., "Progesterone Promotes Differentiation of Human Cord Blood Fetal T Cells into T Regulatory Cells but Suppresses Their Differentiation into Th17 Cells," J Immunol., 2011, 187:1778-1787.
Lesniewski et al., "BACH2 Directly Regulates Expression of Foxp3 in UCB CD4+ T-Cells," Blood Journal, 2008, 5 pages.

(Continued)

*Primary Examiner* — Michail A Belyavskyi
(74) *Attorney, Agent, or Firm* — Eversheds-Sutherland (US) LLP

(57) ABSTRACT

Methods for producing therapeutic T cells from umbilical cord blood are provided. Methods for treating immune-related diseases or conditions (e.g. autoimmune diseases, transplant rejection, cancer) using umbilical cord blood derived therapeutic T cells are also provided. Compositions comprising umbilical cord blood derived therapeutic T cells are also provided.

17 Claims, 26 Drawing Sheets

(56) References Cited

OTHER PUBLICATIONS

Mehrasa et al., "Mesenchymal Stem Cells as a Feeder Layer Can Prevent Apoptosis of Expanded Hematopoietic Stem Cells Derived from Cord Blood," Int. J. Mol. Cell. Med., 2014, 3(1), 10 pages.
Zhao et al., "Virus-Specific Regulatory T Cells Ameliorate Encephalitis by Repressing Effector T Cell Functions from Priming to Effector Stages," PLOS Pathogens, 2014, 10(8):e1004279, 13 pages.

* cited by examiner

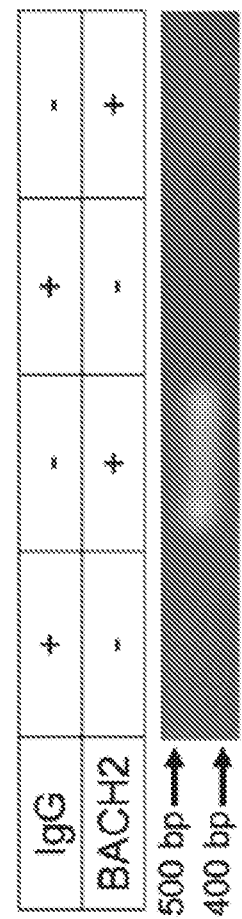
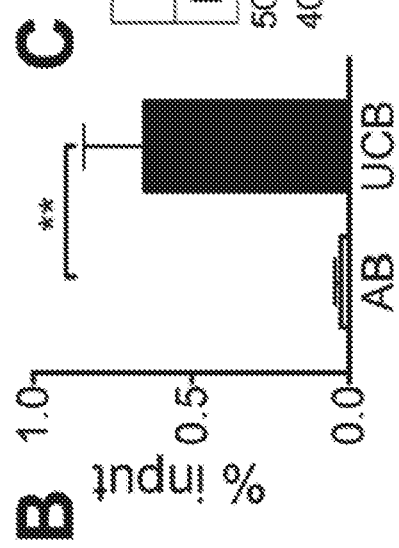
Figures 21A-21C

T CELLS DERIVED FROM UMBILICAL CORD BLOOD

CROSS REFERENCE TO RELATED APPLICATIONS

This application claims priority benefit of PCT/US2018/015667, filed Jan. 29, 2018, which claims priority benefit of U.S. Provisional Application Nos. 62/451,364, 62/552,119, and 62/595,243, filed Jan. 27, Aug. 30, and Dec. 6, 2017, respectively. The entire contents of which are incorporated by reference herewith.

FIELD OF THE INVENTION

The present disclosure relates generally to methods for producing T cells and compositions concerning the same. The present disclosure also relates to methods for adoptively transferring T cells to treat an immune-related disease or condition, and compositions comprising the same.

BACKGROUND

Adoptive cell immunotherapy is an emerging strategy to treat a variety of immune-related diseases and conditions, and involves administering immune system derived cells with the goal of improving immune functionality and characteristics. Adoptive cell immunotherapy typically requires extracting T cells from a subject, modifying and/or expanding the cells ex vivo, and then introducing the modified and/or expanded T cells into a patient. The application of adoptive cell immunotherapy has been constrained by the ability to isolate, differentiate, modify, and/or expand functional T cells having desired phenotypes and characteristics ex vivo. Therefore, the transition of adoptive cell immunotherapy from a promising experimental regimen to an established standard of care treatment relies largely on the development of safe, efficient, robust, and cost-effective cell manufacturing protocols. A T cell manufacturing protocol having general applicability is particularly desirable because there are many types of T cell populations, such as inducible regulatory T cells, chimeric antigen receptor-expressing T cells, and virus specific effector T cells, which are suitable for use in adoptive cell immunotherapy.

The present background discusses inducible regulatory T cells as representative example of therapeutic T cells and the needs for improved methods of producing therapeutic T cells suitable for use in adoptive cell immunotherapy. There are other types of therapeutic T cells that are suitable for use in adoptive cell immunotherapy, such as chimeric antigen receptor-expressing T cells (CAR-Ts) and virus specific effector T cells, and these other types of therapeutic T cells would also benefit from improved methods of producing therapeutic T cells.

The immune system is finely tuned to efficiently target a broad array of diverse pathogens and keep cancer cells in check, while avoiding reactions against self. To control autoimmunity, humans, similar to all mammals, have developed a number of suppressor cell populations. Among these, regulatory T cells (Tregs) have emerged as the major cell subset maintaining tolerance, with the ability to potently suppress the activation and effector function of other immune cells, including CD4+ and CD8+ T cells, B cells, NK cells, macrophages, and dendritic cells.

Regulatory T cells encompass various subsets of CD4+ and CD8+ cells. In general, these subsets are classified according to their site of development and/or the cytokines they produce. One subset of regulatory T cells develops in the thymus (natural regulatory T cells or "nTreg") while a different subset develops in the periphery when naïve CD4+ T cells encounter antigen and differentiate into inducible regulatory T cells ("iTregs") in the presence of TGF-β, IL-10 and IL-2. Both regulatory T cell populations control naïve and ongoing immune responses through a number of independent pathways ranging from direct cell-cell interactions to indirect suppression mediated by soluble cytokines (e.g. IL-10, IL-35 and TGF-β), and metabolic controls. The consequence of these activities is to reduce effector T cell function and promote immune tolerance.

Since regulatory T cells control pathogenic self-reactive cells, they have therapeutic potential for treating autoimmune diseases as well as suppressing inflammatory conditions (e g immune rejection in stem cell, tissue, and organ transplantation, as well as adverse graft vs. host disease). Among the regulatory T cell subsets, $CD4^+CD25^+Foxp3^+$ iTregs offer a promising immunomodulatory treatment strategy due to their role in preventing autoimmunity and enhancing tolerance. The low number of nTregs in human peripheral blood as well as the low proliferative potential of nTregs remain significant challenges to broader clinical applications and make them less desirable than iTregs.

Inducible Treg (iTreg) can reestablish tolerance in settings where nTreg are decreased or defective. However, clinical implementation of their potent immune regulatory activity by collection, manufacturing, and dosing quantity and frequency of autologous (self) and allogeneic (other) iTreg in vivo administration has proven challenging. More specifically, experience to date with autologous iTregs has been challenged with the difficulty to expand from the small numbers that can generally be isolated from the peripheral blood, and their functional properties decrease during ex vivo expansion. Moreover, the instability of expression of Forkhead box P3 (FOXP3) transcription factor that is important for iTreg differentiation and function has to date posed a significant barrier to iTreg clinical application.

FOXP3 is a member of the forkhead/winged-helix family of DNA binding transcription factors and is the master regulator for the development and maintenance of regulatory $CD4^+25^{high}$ Treg. Deletion or mutation of the FOXP3 gene in either mice or in humans can result in severe autoimmune disease, attributable to Treg deficiency. Activated protein 1 (AP-1), Nuclear factor of activated T-cells 1 (NFAT1), Nuclear factor-KB (NF-kB), Small mothers against decapentaplegic 2 (smad2), smad3, and signal transducer and activator of transcription 5 (STAT5) all have been identified as regulators of FOXP3 mRNA expression. In addition, stable FOXP3 expression is associated with epigenetic regulatory control in mice.

The regulation of FOXP3 expression in human $CD4^+$ T-cells is not fully elucidated. Human FOXP3 is expressed by activated $CD4^+$ and $CD8^+$ T-cells as a possible negative feedback loop on cytokine production. In addition, human $CD4^+$ T-cells have two splice variants of FOXP3 mRNA while there is only one version in mice. Both human FOXP3 splice variants are co-expressed and no known functional difference has been determined.

Some prior methods have produced autologous iTregs ex vivo by isolating peripheral blood mononuclear cells from blood, stimulating the peripheral blood mononuclear cell population with an antigen to produce iTregs, and recovering and expanding the iTregs. The clinical efficacy of these cells, when transferred to a patient, is hampered by the acquisition of terminal effector differentiation and exhaustion features during expansion ex vivo, thus preventing their function and persistence in vivo. Specifically, large scale ex vivo T-cell expansion and effector differentiation can lead to not only robust antigen-specific cytolysis but also to terminal effector differentiation and poor capacity to further expand and persist in vivo. Accumulating evidence suggests that optimal therapeutic effects are achieved when ex vivo generated T cells maintain features associated with early naïve phenotype. Hence, a compromise must be sought to ensure efficient antigen priming while limiting T cell differentiation during the culture period.

Therefore, new methods are needed for producing, ex vivo, non-exhausted iTregs that maintain an immature phenotype. New methods are also needed for treating an inflammatory or an autoimmune condition (e.g. autoimmune diseases, transplant rejection, and graft vs. host disease). New iTreg compositions expanded ex vivo in such manner to render sufficient numbers to expectedly have in vivo therapeutic effect whilst maintaining an immature phenotype and lacking exhaustion features are also needed.

More generally, new methods are needed for producing, ex vivo, therapeutic T cells having suitable characteristics (e.g. immature phenotypes, lack of exhaustion features, etc.). New methods are also needed for treating immune-related diseases or conditions with adoptively transferred therapeutic T cells. New therapeutic T cell compositions comprising therapeutic T cells manufactured and/or expanded ex vivo, and which have in vivo therapeutic effect whilst maintaining suitable characteristics (e.g. immature phenotypes, lack of exhaustion features, etc.), are also needed.

SUMMARY OF THE INVENTION

Methods for producing inducible regulatory T cells from blood are provided. In embodiments, the blood may be obtained from sourced from umbilical cord or adult pheresis, for example. In certain embodiments, the methods for producing inducible regulatory T cells from blood includes: providing blood; isolating naïve CD4+ T cells from the blood; inducing the naïve CD4+ T cells to differentiate into a first composition comprising iTregs; separating the iTregs from the first composition to form a substantially purified iTreg composition; and expanding the purified iTreg composition over a mesenchymal stromal cell (MSC) feeder layer to form an expanded iTreg composition.

Methods for treating an inflammatory or an autoimmune condition (e.g. autoimmune diseases, transplant rejection, and graft vs. host disease) using blood derived inducible regulatory T cells expanded over mesenchymal stromal cells are also provided. In certain embodiments, the methods for treating an inflammatory or an autoimmune condition in a subject in need thereof includes: administering to the subject a composition comprising a therapeutically effective dose of blood derived iTregs expanded over mesenchymal stromal cells.

Compositions comprising umbilical cord blood or adult blood derived inducible regulatory T cells expanded over mesenchymal stromal cells are also provided.

Methods for producing therapeutic T cells from umbilical cord blood or adult blood are provided. In certain embodiments, the methods for producing therapeutic T cells from umbilical cord blood or adult blood include: providing umbilical cord blood or adult blood; isolating naïve CD4+ T cells from the umbilical cord blood or adult blood; and manufacturing a therapeutic T cell composition from the isolated naïve CD4+ T cells. In certain embodiments, the manufacturing step comprises culturing the therapeutic T cell composition, or a precursor thereto, over a mesenchymal stromal cell (MSC) feeder layer.

In certain embodiments, the methods and manufacturing steps comprise inducing BACH2 transcriptional regulation to increase expression of Fox3P, by methods such as, but not limited to, gene transduction via lentiviral transduction or electroporation.

Methods for treating an immune-related disease or condition are also provided. In certain embodiments, the methods for treating an immune-related disease or condition in a subject in need thereof include: administering to the subject a composition comprising a therapeutically effective dose of a blood derived therapeutic T cell composition, wherein the blood derived therapeutic T cell composition or a precursor thereto was cultured over a mesenchymal stromal cell (MSC) feeder layer.

Compositions comprising umbilical cord or adult blood derived therapeutic T cells, wherein the umbilical cord or adult blood derived therapeutic T cells or a precursor thereto were cultured over a mesenchymal stromal cell (MSC) feeder layer, are also provided.

BRIEF DESCRIPTION OF THE DRAWINGS

FIG. 2 shows cells at day four of stimulation.

FIG. 3 shows relative expansion between day zero and day four of anti-CD2/3/28 stimulation in the presence of TGFβ1.

FIG. 6A shows that UCB derived iTregs have higher modulation of dendritic cells relative to PBMC derived iTregs. FIG. 6B shows that UCB derived iTregs have higher metabolic disruption relative to PBMC derived iTregs.

FIG. 13A shows Bach2 expression in CD4*CD45RA* adult and UCB CD4 T cells was measured by western blot analysis. FIG. 13B shows inducible regulatory T cells were generated in AB and UCB naïve CD4 T cells. Foxp3 expression was measured in 4 days after stimulation by FACS analysis (AB, n=9; UCB, n=12). FIG. 13C shows Bach2 protein expression in adult and UCB CD4 T cells measured by western blot analysis 4 days later after stimulation. Images are representative of multiple western blots. Data are from multiple experiments (n=4-8). * $p<0.01$, unpaired Student t test.

In FIG. 14A, UCB CD4 T cells were transfected with BACH2 shRNA or control shRNA. Four days post-transfection an aliquot of cells was harvested and the cells were measured BACH2 expression by FACS analysis. Results are the average of 4 different knockdown transfections with 3 different UCB units. FIG. 14B shows T cells transfected with BACH2 shRNA and control shRNA CD4 T cells. Foxp3 expression was measured 4 days after transfection by FACS analysis. Figures are representative of four different experiments. * $p<0.05$, unpaired Student t test.

In FIG. 15A inducible regulatory T cells were generated in AB and UCB naïve CD4 T cells. CTLA-4, CD39 and CD73 were measured 4 days after stimulation by FACS analysis (AB, n=5; UCB, n=7). FIG. 15B shows a suppressive functional assay. Suppressive function was subsequently determined by FACS analysis. Data are from three independent experiments (n=5).  $p<0.01$, * $p<0.001$, unpaired Student t test.

In FIG. 16A Foxp3 expression was measured at 14 days after rested in media and MSC platform conditions. FIG. 15B shows time kinetic assay of Foxp3 stability. In FIG. 15C IFNγ and IL-17A was measured from UCB iTreg cells after expanded over media and MSC platform. In FIG. 15D UCB iTreg cells were examined for suppressive function. Suppressive function was subsequently determined by CFSE analysis. Data are from three independent experiments (n=4.5). ** $p<0.01$, unpaired Student t test.

FIGS. 21A-21C show that BACH2 binds to the FOXP3 promoter in TGF-β induced FOXP3+ UCB iTregs. (A) Location of putative BACH2 DNA binding sites in the FOXP3 promoter with similarity to the AP-1 DNA binding consensus sequence, and their relative position to NFAT1 DNA binding sites and the 450 bp amplicon. BACH2 DNA binding sites within the FOXP3 promoter aligned with the AP-1 DNA consensus sequence (underlined), BACH2 DNA consensus sequence (italic), and distance from NFAT1 DNA binding sites (gray). (B) ChIP assays for BACH2 in TGF-β induced AB and UCB FOXP3+ T cells. Data are from 3-5 individual samples. Each sample was analyzed in duplicate. Background was determined using the IgG control group. ** $p<0.01$, unpaired Student t test. (C) Gel image of PCR amplification of the FOXP3 promoter from BACH2 IP and IgG control samples.

FIGS. 23A-23-B show Comparison of inhibitory molecules expression on UCB CD4+ CD127lowCD25+ natural Treg and iTreg cells. (A) Gating note for nTreg sort from UCB. (B) Surface and cytoplasmic (CTLA-4) staining in nTreg and iTreg. 1-5×105 cells were stained with each antibody. Expression was measured by FACS analysis (n=3-5).

DETAILED DESCRIPTION

I. Overview

Figure 1:
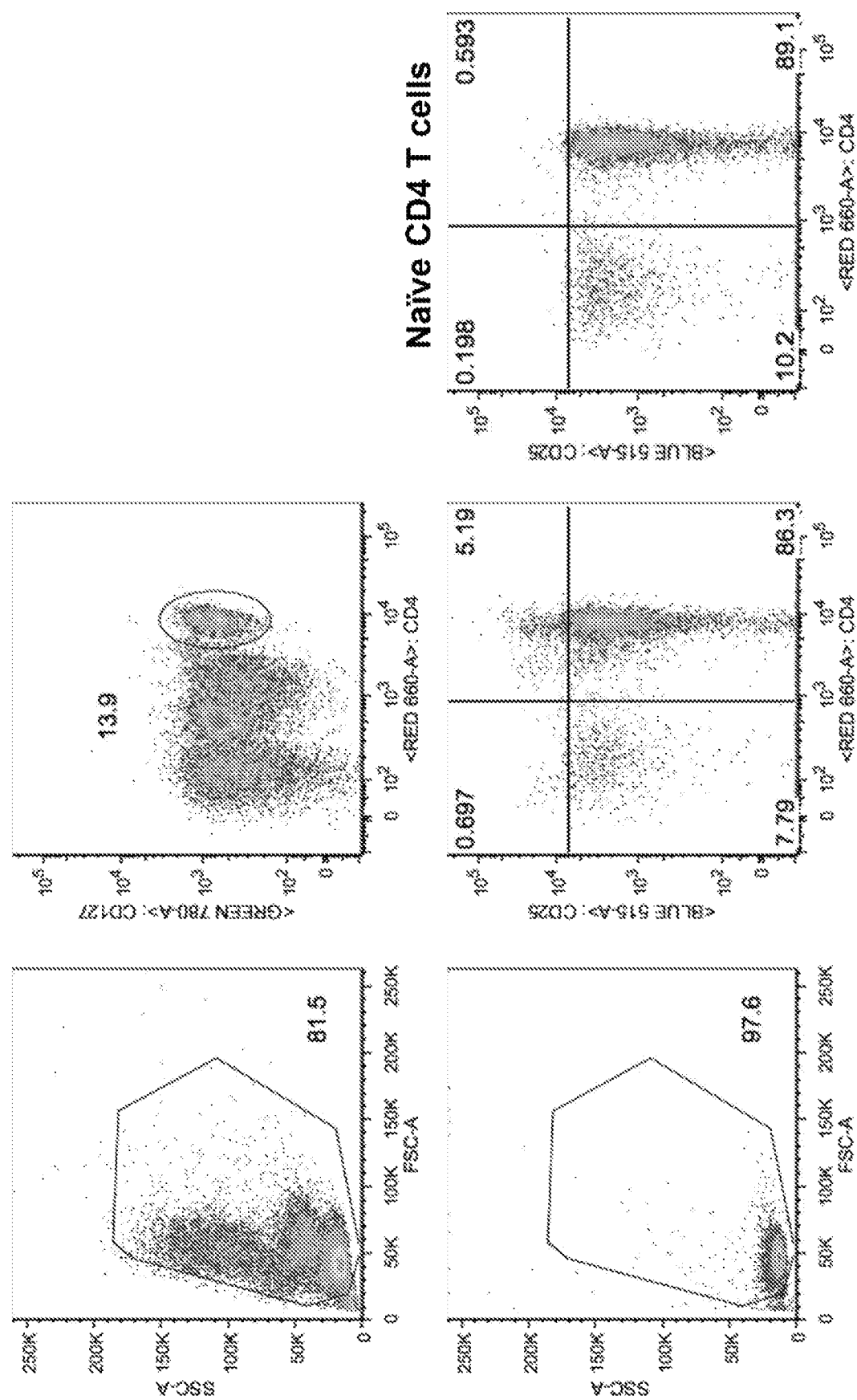
FIG. 1 shows naïve CD4+ T cell enrichment from umbilical cord blood. Naïve CD4+ T cells were purified from umbilical cord blood using density gradient separation (Ficoll) and magnetic cell isolation and separation (MACS).

Methods for producing therapeutic T cells from umbilical cord or adult blood blood are provided. Methods for treating an immune-related disease or condition using therapeutic T cells produced by the methods disclosed herein are also provided. Compositions comprising therapeutic T cells produced by the methods disclosed herein are also provided.

Methods for producing iTregs from umbilical cord blood or adult bllod are provided. Methods for treating an inflammatory or an autoimmune condition (e.g. autoimmune diseases, transplant rejection, and graft vs. host disease) using iTregs produced by the methods disclosed herein are also provided. Compositions comprising iTregs produced by the methods disclosed herein are also provided.

The present methods and compositions incorporate several observations. First, the youngest, most primitive naïve CD4$^+$ T cells can be obtained from umbilical cord blood. Second, naturally occurring Treg cells are actively trafficked to and retained in bone marrow during homeostasis, and bone marrow may function as an immune regulatory organ via Treg recruitment and retention. Because Tregs are retained in bone marrow during homeostasis, bone marrow and/or its constituent cells can provide molecular signals that discourage Tregs from differentiating into a more mature phenotype and exhibiting markers associated with T cell exhaustion during homeostasis. It has been surprisingly found that deriving iTregs from UCB CD4$^+$ T cells and expanding those iTregs over mesenchymal stromal cells (MSCs), a cell type native to bone marrow, results in iTregs that maintain a more primitive phenotype and express fewer surface antigens indicative of T cell maturation and/or exhaustion. It has also been surprisingly found that deriving therapeutic T cells from umbilical cord blood (UCB) CD4$^+$ T cells and manufacturing, culturing, and/or expanding those therapeutic T cells or a cellular precursor thereto over mesenchymal stromal cells (MSCs), a cell type native to bone marrow, results in therapeutic T cells that maintain a more primitive phenotype and express fewer surface antigens indicative of T cell maturation and/or exhaustion than do T cells derived from adult peripheral blood.

It has also been surprisingly found that molecular transcriptional regulation of UCB CD4+45RA+ T cells differs from that of adult peripheral blood CD4+ CD45RA+ T cells, and that this difference is beneficial to the number and function of Foxp3+ iTreg differentiated in standard conditions. In embodiments, transcription factor 'broad complex-Tramtrack-Bric-a-brac domain (BTB) and Cap'n'collar (CNC) homology 1, basic leucine zipper transcription factor 2' (BACH2) enhances iTreg generation by regulation of Foxp3 expression integral to the suppressive function of UCB-derived iTregs.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "aberrant immune response" refers to inappropriately regulated immune responses that lead to patient symptoms. Aberrant immune responses can include the failure of a subject's immune system to distinguish self from non-self (e.g. autoimmunity), the failure to respond appropriately to foreign antigens, hyperimmune responses to foreign antigens (e.g. allergic disorders), and undesired immune responses to foreign antigens (e.g. immune rejections of cell, tissue, and organ transplants, and graft vs. host disease).

As used herein, the term "antigen" embraces any molecule capable of generating an immune response. In the context of autoimmune disorders, the antigen is a self-antigen.

As used herein, "immune response" embraces a subject's response to foreign or self antigens. The term includes cell mediated, humoral, and inflammatory responses.

As used herein, "inappropriately regulated" embraces the state of being inappropriately induced, inappropriately suppressed, non-responsiveness, undesired induction, undesired suppression, and/or undesired non-responsiveness.

As used herein, "patient" or "subject" means an animal subject to be treated, with human patients being preferred.

As used herein, "proliferation" or "expansion" refers to the ability of a cell or population of cells to increase in number.

As used herein, a composition containing a "purified cell population" or "purified cell composition" means that at least 30%, 50%, 60%, typically at least 70%, and more preferably 80%, 90%, 95%, 98%, 99%, or more of the cells in the composition are of the identified type.

As used herein, the term "regulatory T cell" embraces T cells that express the $CD4^+CD25^+Foxp3^+$ phenotype.

As used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances. In one aspect, at least 30%, 50%, 60%, 70%, 80%, 90%, 95%, 98%, 99%, or more of the second substance is removed from the first substance.

The terms "suppression," "inhibition" and "prevention" are used herein in accordance with accepted definitions. "Suppression" results when an ongoing immune response is blocked or significantly reduced as compared with the level of immune response that results absent treatment (e.g., by the iTreg cells disclosed herein). Similarly, "inhibition" refers to blocking the occurrence of an immune response or significantly reducing such response as compared with the level of immune response that results absent treatment (e.g., by the iTreg cells disclosed herein). When administered prophylactically, such blockage may be complete so that no targeted immune response occurs, and completely blocking the immune response before onset is typically referred to as a "prevention."

As used herein, "therapeutically effective" refers to an amount of cells that is sufficient to treat or ameliorate, or in some manner reduce the symptoms associated with an aberrant immune response. When used with reference to a method, the method is sufficiently effective to treat or ameliorate, or in some manner reduce the symptoms associated with an aberrant immune response. For example, an effective amount in reference to a disease is that amount which is sufficient to block or prevent its onset; or if disease pathology has begun, to palliate, ameliorate, stabilize, reverse or slow progression of the disease, or otherwise reduce pathological consequences of the disease. In any case, an effective amount may be given in single or divided doses.

As used herein, the term "treatment" embraces at least an amelioration of the symptoms associated with the aberrant immune response in the patient, where amelioration is used in a broad sense to refer to at least a reduction in the magnitude of a parameter, e.g. a symptom associated with the condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

II. Methods for Generating iTregs

Methods are provided for generating iTregs. In embodiments, the methods comprise one or more of the following steps: providing umbilical cord blood; isolating naïve CD4+ T cells from the umbilical blood; inducing the naïve CD4+ T cells to differentiate into a first composition comprising iTregs; separating the iTregs from the first composition to form a substantially purified iTreg composition; and expanding the purified iTreg composition over a mesenchymal stromal cell (MSC) feeder layer to form an expanded iTreg composition.

In some embodiments, umbilical cord blood can originate from a variety of animal sources including, for example, humans. Thus, some embodiments can include providing human umbilical cord blood.

In some embodiments, naïve CD4+ T cells are separated/isolated from umbilical cord blood. In some embodiments, naïve CD4+ T cells are substantially separated from other cells in umbilical cord blood to form a purified naïve CD4+ T cell composition. Methods for separating/purifying naïve CD4+ T cells from blood are well known in the art. Exemplary techniques can include Ficoll-Paque density gradient separation to isolate viable mononuclear cells from blood using a simple centrifugation procedure, and affinity separation to separate naïve CD4+ T cells from the mononuclear cells. Exemplary affinity separation techniques can include, for example, magnetic separation (e.g. antibody-coated magnetic beads) and fluorescence-activated cell sorting. In one non-limiting example, mononuclear cells can be obtained from umbilical cord blood by gradient density separation using Ficoll. Non-desired cells (i.e. non CD4+ T cells) from the mononuclear cell fraction can be labeled with biotinylated anti-CD45RO antibodies and magnetically separated/depleted using magnetically assisted cell sorting ("MACS"), leaving behind an enriched/purified population of naïve CD4+ T cells. In some embodiments, at least 75%, 85%, 86%, 87%, 88%, 89%, 90%, 91%, 92%, 93%, 94%, 95%, 96%, 97%, 98%, 99%, or more of the cells of the resulting composition are naïve CD4+ T cells. In some embodiments, the purity of naïve CD4+ T cells is equal to or greater than 75%, 85%, 86%, 87%, 88%, 89%, 90%, 91%, 92%, 93%, 94%, 95%, 96%, 97%, 98%, 99%, or more.

In some embodiments, the purified population of naïve CD4+ T cells are induced to render a first composition comprising iTregs. The naïve T cells can be stimulated to render iTregs using methods well known in the art. One exemplary technique for stimulating naïve CD4+ T cells to render iTregs includes culturing naïve CD4+ T cells with Dynabeads (anti-CD3, anti-CD28) at a 1:1 ratio in IL-2 (100 U/ml) and TGF-β1 (5 ng/ml). Activated CD4+ T cells can be harvested and washed after a suitable period of time such as, for example, 96 hours of these stimulation methods.

In some embodiments, iTregs are separated/isolated from the first composition comprising iTregs to form a substantially purified iTreg composition. In some embodiments, iTregs are substantially separated from other cells in the first composition comprising iTregs to form a substantially purified iTreg composition. Methods for separating/purifying/enriching iTregs are well known in the art. Exemplary techniques can include affinity separation methods such as magnetic cell sorting (e.g. antibody-coated magnetic beads) and fluorescence-activated cell sorting to separate iTregs from other cells. In one non-limiting example, iTregs are purified using magnetic separation kits. In some embodiments, at least 75%, 85%, 86%, 87%, 88%, 89%, 90%, 91%, 92%, 93%, 94%, 95%, 96%, 97%, 98%, 99%, or more of the cells of the substantially purified iTreg composition are iTregs. In some embodiments, the purity of iTregs is equal to or greater than 75%, 85%, 86%, 87%, 88%, 89%, 90%, 91%, 92%, 93%, 94%, 95%, 96%, 97%, 98%, 99%, or more. In some embodiments, at least 75%, 85%, 86%, 87%, 88%, 89%, 90%, 91%, 92%, 93%, 94%, 95%, 96%, 97%, 98%, 99%, or more of the cells of the substantially purified iTreg composition are $CD4^+CD25^+Foxp3^+$.

In some embodiments, the purified iTreg composition is expanded over a mesenchymal stromal cell (MSC) feeder layer to form an expanded iTreg composition. Thus, in embodiments, the purified iTreg composition is expanded to produce a larger population of iTregs. The expansion step can use culture techniques and conditions well known in the art. In certain embodiments, the iTregs are expanded by maintaining the cells in culture for about 1 day to about 3 months. In further embodiments, the iTregs are expanded in culture for about 2 days to about 2 months, for about 4 days to about 1 month, for about 5 days to about 20 days, for about 6 days to about 15 days, for about 7 days to about 10 days, and for about 8 days to about 9 days. The mesenchymal stromal cells (MSC) can come from any suitable source (e.g. bone marrow, adipose tissue, placental tissue, umbilical cord blood, umbilical cord tissue).

In some embodiments, the cultured iTregs are expanded at least 2-fold, at least 3-fold, 4, 5, 6, 7, 8, 9, 10, 50, 100, 200, 300, 500, or at least 800-fold. In some embodiments, compositions comprising the expanded iTregs contain a clinically relevant number or population of iTreg cells. In some embodiments, compositions include about $10^3$, about $10^4$, about $10^5$ cells, about $10^6$ cells, about $10^7$ cells, about $10^8$ cells, about $10^9$ cells, about $10^{10}$ cells or more. In some embodiments, the number of cells present in the composition will depend upon the ultimate use for which the composition is intended, e.g., the disease or state or condition, patient condition (e.g., size, weight, health, etc.), and other health-related parameters that a skilled artisan would readily understand. In addition, in some embodiments, the clinically relevant number of cells can be apportioned into multiple infusions that cumulatively equal or exceed the desired administration, e.g., $10^9$ or $10^{10}$ cells.

In embodiments, transcription factor 'broad complex-Tramtrack-Bric-a-brac domain (BTB) and Cap'n'collar (CNC) homology 1, basic leucine zipper transcription factor 2' (BACH2) is combined with an ex vivo culture of UCB-derived iTregs to enhance iTreg generation by regulation of Foxp3 expression and the suppressive function of UCB-derived iTregs.

The substantially purified iTregs can be used immediately. The substantially purified iTregs can also be frozen at liquid nitrogen temperatures and stored for long periods of time, being thawed and capable of being used. The cells may be stored, for example, in DMSO and/or FCS, in combination with medium, glucose, etc.

III. Exemplary Uses of iTregs Generated According to the Present Methods

Methods are provided for treating an inflammatory or an autoimmune condition in a subject in need thereof. In embodiments, the methods comprise administering to the subject a composition comprising a therapeutically effective dose of umbilical cord blood derived iTregs expanded over mesenchymal stromal cells.

In some embodiments, the compositions of the present disclosure comprising umbilical cord blood derived iTregs expanded over mesenchymal stromal cells are useful for suppression of immune function in a patient. For example, autologous cells may be isolated, expanded and cultured in vitro as described herein, and subsequently administered to the patient. In some embodiments, such treatment is useful, for example, to down-regulate harmful T cell responses to self and foreign antigens, and/or to induce long term tolerance.

In some embodiments, a therapeutically effective amount of a composition comprising umbilical cord blood derived iTregs expanded over mesenchymal stromal cells can be administered to the subject with a pharmaceutically acceptable carrier. Administration routes may include any suitable means, including, but not limited to, intravascularly (intravenously or intra-arterially). In some embodiments, a preferred administration route is by IV infusion. In some embodiments, the particular mode of administration selected will depend upon the particular treatment, disease state or condition of the patient, the nature or administration route of other drugs or therapeutics administered to the subject, etc.

In some embodiments, about $10^5$-$10^{11}$ cells can be administered in a volume of a 5 ml to 1 liter, 50 ml to 250 ml, 50 ml to 150, and typically 100 ml. In some embodiments, the volume will depend upon the disorder treated, the route of administration, the patient's condition, disease state, etc. The cells can be administered in a single dose or in several doses over selected time intervals, e.g., to titrate the dose.

In one aspect, the compositions and methods disclosed herein are directed to modulating an aberrant immune response in a subject, such as an autoimmune disorder or an allergy, by administering the umbilical cord blood derived iTregs expanded over mesenchymal stromal cells disclosed herein. In some embodiments, the subject is suffering from an autoimmune disorder or an allergic response, and the umbilical cord blood derived iTregs expanded over mesenchymal stromal cells are used to treat the autoimmune disorder or allergic disorder. In some embodiments, the subject is a human afflicted with an autoimmune disorder or allergic disorder.

The umbilical cord blood derived iTregs expanded over mesenchymal stromal cells disclosed herein can be used to treat, alleviate or ameliorate the symptoms of or suppress a wide variety of autoimmune disorders. In some embodiments, the autoimmune disorders including, but are not limited to, Addison's disease, Alopecia universalis, ankylosing spondylitis, antiphospholipid antibody syndrome, aplastic anemia, asthma, autoimmune hepatitis autoimmune infertility, autoimmune thyroiditis, autoimmune neutropenia, Behcet's disease, bullous pemphigoid, Chagas' disease, cirrhosis, Coeliac disease, colitis, Crohn's disease, Chronic fatigue syndrome, chronic active hepatitis, dense deposit disease, discoid lupus, degenerative heart disease, dermatitis, insulin-dependent diabetes mellitus, dysautonomia, endometriosis, glomerulonephritis, Goodpasture's disease, Graves' disease, graft versus host disease (GVHD), graft rejection in a recipient following solid organ (e.g., heart, liver, kidney, lung), tissue, bone marrow, or stem cell transplantation, Graves' disease, Guillain-Barre syndrome, Hashimoto's disease, hemolytic anemia, Hidradenitis suppurativa, idiopathic thrombocytopenia purpura, inflammatory bowel disease ("IBD"), insulin dependent diabetes mellitus, interstitial cystitis, mixed connective tissue disease, multiple sclerosis ("MS"), myasthenia gravis, neuromyotonia, opsoclonus myoclonus syndrome, optic neuritis, Ord's thyroiditis, pemphigus vulgaris, pernicious anemia, polyarthritis, polymyositis, primary biliary cirrhosis, psoriasis, Reiter's syndrome, rheumatoid arthritis ("RA"), sarcoidosis, scleroderma, Sjogren's syndrome, systemic lupus erythematosus, Takayasu's arteritis, temporal arteritis, thrombocytopenia purpura, ulcerative colitis, vitiligo, vulvodynia, warm autoimmune hemolytic anemia, or Wegener's granulomatosis.

Additionally or alternatively, in some embodiments, the umbilical cord blood derived iTregs expanded over mesenchymal stromal cells disclosed herein can be used to treat, alleviate or ameliorate the symptoms of or suppress a wide variety of immune related diseases or conditions. In some embodiments, the immune related disease or condition includes, without limitation, allergic conjunctivitis, allergic rhinitis, allergic contact dermatitis, anaphylactoid purpura, asthma, erythema elevatum diutinum, erythema marginatum, erythema multiforme, allergic granulomatosis, granuloma annulare, granlocytopenia, hypersensitivity pneumonitis, keratitis, nephrotic syndrome, overlap syndrome, pigeon breeder's disease, pollinosis, idiopathic polyneuritis, urticaria, uveitis, juvenile dermatomyositis, acute disseminated encephalomyelitis (adem), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, bullous pemphigoid, cancer, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, crest syndrome, Crohn's disease, Cushing's Syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressiva, fibrosing alveolitis (idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis (gestational pemphigoid), hidradenitis suppurativa, Hughes-Stovin syndrome, hypogammaglobulinemia, idiopathic inflammatory demyelinating diseases, idiopathic pulmonary fibrosis, idiopathic thrombocytopenic purpura (autoimmune thrombocytopenic purpura), IgA nephropathy, inclusion body myositis, chronic inflammatory demyelinating polyneuropathy, interstitial cystitis, juvenile idiopathic arthritis (juvenile rheumatoid arthritis), Kawasaki's disease, Lambert-Eaton myasthenic syndrome, leukocytoclastic vasculitis, lichen planus, lichen sclerosus, linear IgA disease (lad), Lou Gehrig's disease (Amyotrophic lateral sclerosis), lupoid hepatitis (autoimmune hepatitis), lupus erythematosus, Majeed syndrome, Méniére's disease, microscopic polyangiitis, Miller-Fisher syndrome (Guillain-Barre Syndrome), mixed connective tissue disease, morphea, Mucha-Habermann disease (Pityriasis lichenoides et varioliformis acuta), multiple sclerosis, myasthenia gravis, myositis, narcolepsy, neuromyelitis optica (devic's disease), neuromyotonia, occular cicatricial pemphigoid, opsoclonus myoclonus syndrome, Ord's thyroiditis, palindromic rheumatism, pandas (pediatric autoimmune neuropsychiatric disorders associated with streptococcus), paraneoplastic cerebellar degeneration, paroxysmal nocturnal hemoglobinuria (pnh), Parry Romberg syndrome, Parsonage-Turner syndrome, pars planitis, pemphigus vulgaris, pernicious anaemia, perivenous encephalomyelitis, poems syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome, Schnitzler syndrome, scleritis, scleroderma, serum sickness, Sjogren's syndrome, spondyloarthropathy, Still's disease (Juvenile Rheumatoid Arthritis), stiff person syndrome, subacute bacterial endocarditis (sbe), Susac's syndrome, Sweet's syndrome, Sydenham chorea see PANDAS, sympathetic ophthalmia, systemic lupus erythematosus, Takayasu's arteritis, temporal arteritis (giant cell arteritis), thrombocytopenia, Tolosa-Hunt syndrome, transverse myelitis, ulcerative colitis, undifferentiated connective tissue disease, undifferentiated spondyloarthropathy, urticarial vasculitis, vasculitis, vitiligo, wegener's granulomatosis, graft versus host disease (GVHD).

In some embodiments, the umbilical cord blood derived iTregs expanded over mesenchymal stromal cells disclosed herein can be used to treat, alleviate or ameliorate the symptoms of or suppress a wide variety of allergic disorders including, but not limited to, allergic conjunctivitis, allergic rhinitis, allergic contact dermatitis, alopecia universalis, anaphylactoid purpura, asthma, atopic dermatitis, dermatitis herpetiformis, erythema elevatum diutinum, erythema marginatum, erythema multiforme; erythema nodosum, allergic granulomatosis, granuloma annulare, granlocytopenia, hypersensitivity pneumonitis, keratitis, neplirotic syndrome, overlap syndrome, pigeon breeder's disease, pollinosis, idiopathic polyneuritis, urticaria, uveitis, juvenile dermatomyositisitis, and vitiligo.

In some embodiments, the umbilical cord blood derived iTregs expanded over mesenchymal stromal cells disclosed herein can be introduced into the subject to treat or modulate an autoimmune disorder or allergic disorder. For example, the subject may be afflicted with a disease characterized by having an ongoing or recurring autoimmune reaction or allergic reaction. In some embodiments, the modulating comprises inhibiting the autoimmune reaction or allergic reaction.

In some embodiments, umbilical cord blood derived iTregs expanded over mesenchymal stromal cells disclosed herein can be administered to a subject for immunotherapy, such as, for example, in tumor surveillance, immunosuppression of cancers such as solid tumor cancers (e.g., lung cancer), and the suppression of in vivo alloresponses and autoimmune responses, including but not limited to, graft versus host disease (GVHD).

The subject methods find use in the treatment of a variety of different conditions and transplant situations in which the modulation of an aberrant immune response in a patient is desired. By way of example, but not by way of limitation, in the case of cellular, tissue, or organ transplantation, a composition comprising umbilical cord blood derived iTregs expanded over mesenchymal stromal cells as disclosed herein may be administered during the time of surgery to prevent graft versus host disease in a transplant patient. To keep the cells at the site until completion of the surgical procedure, in some embodiments, it is convenient to administer the cells in a pharmaceutically acceptable carrier, such as an artificial gel, or in clotted plasma, or by utilizing other controlled release mechanism known in the art.

EXAMPLES

Example 1: Generating Inducible Regulatory T Cells (iTregs) from Umbilical Cord Blood Methods Protocol for isolating naïve CD4+ T cells from umbilical cord blood
1. Add density gradient medium (GE Healthcare, Cat#: 17-1440-03) to the 50 ml SepMate™ tube (STEMCELL technologies, Cat#: REF 85450) by carefully pipetting it through the central hole of the SepMate™ insert. The top of the density gradient medium will be above the insert. Protocol uses human Naïve CD4 T cell isolation kit (STEMCELL technologies, Cat#19555) and EasySep Violet Magnet (STEMCELL technologies, Cat#: 103720).
2. Dilute UCB sample with an equal volume of PBS+2% FBS. (PBS 1× w/o Ca, w/o Mg (CCF Media Lab 121-1000p, Lot#262); Fetal Bovine Serum (CCF Media Lab PBS-500HI)). Mix gently.
3. Keeping the SepMate™ tube vertical, add the diluted sample by pipetting it down the side of the tube (no more than 17 ml per tube). The sample will mix with the density gradient medium above the insert.
4. Centrifuge at 1200×g for 15 minutes at room temperature, with the brake on.
5. Pour off the top layer, which contains the enriched MNCs, into a new tube. Do not hold the SepMate™ tube in the inverted position for longer than 2 seconds. That will allow to separate MNC fraction from red blood cells. Spin down MNC fraction at 1000 rpm, 15 min. RT. Resuspend the cell pellet.
6. Wash enriched MNCs with PBS+2% FBS. Repeat wash
7. Count cells in hemocytometer with Trypan-Blue Stain
8. Determine cell number and centrifuge cell suspension at 1,000 rpm for 10 minutes. Aspirate supernatant completely.
9. Resuspend cell pellet in 1 ml of binding buffer (PBS-2% BSA-2 mM EDTA) per $5\times10^7$ total cells in 5 ml tube. (Bovine Serum Albumin (Fisher, Cat#BP9703-100); UltraPure 0.5M EDTA, pH 8.0 (Gibco, Cat#15575-038)).
10. Add 50 ul/ml Biotinylated Anti-CD45RO antibody to sample and add 50 ul/ml Isolation Cocktail to sample
11. Mix and Incubate sample at RT for 5 min.
12. Add 50 ul/ml RapidSpheres™ to sample and incubate at RT for 5 min
13. Add binding buffer up to 2 ml and up and down
14. Place the tube into the magnet and incubate for 5 min
15. Pour the sample into new 5 ml tube and place the tube into magnet and incubate for 5 min
16. Repeat the above step for 2nd separation
17. Harvested cells were counted and set up for iTreg generation (i.e. stimulation).

Protocol for Inducing iTreg Generation
1. $5\times10^5$ cells are incubated with CD2/3/28 coated dynabeads (1:1 ratio) in IL-2 (100 U/ml) added X-VIVO15 media in 48 well plates. (X-VIVO 15 is Serum-free Hematopoietic Cell Medium with Gent, L-Glu, Phen Red).
2. For iTreg generation, TGF-β1 (5 ng/ml) added to the culture.
3. Activated CD4 T cells are harvested and washed at 96 hrs after stimulation.
4. Cells are stained intracellularly for FOXP3 and surface phenotype: CD4, CD27, CD127, CD45RO, and CCR7. (PE-CF594 Mouse Anti-Human CD27 (Cat#: 562297); Alexa Flour 647 Rat Anti-Human CD197 (CCR7) (Cat#: 557734); FITC Mouse Anti-Human CD4 (Cat#: 555346); PE-Cy™7 Mouse Anti-Human CD127 (Cat#: 560822); PE Mouse Anti-Human CD45RO (Cat#: 555493)).

Protocol for iTreg Resting/Expansion Directly Over Human Bone Marrow Derived MSCs
1. At day 4 stimulation, cells are harvested and CD2/3/28 dynabeads removed by magnet. Tube is placed in magnet at 3 min. Cells are washed with PBS and rested in IL-2 added X-VIVO15 media at $2\text{-}5\times10^5$ cells/ml in 24 well plates alone or over $1\times10^5$ seeded MSC
2. At D6 from start of culture (2 days rest after 4 days stimulation), cells are harvested and phenotyped for CD4, CD27, CD127, CD45RO, and CCR7 surface expression. Remaining wells are replenished with IL-2 supplemented X-VIVO15 media.
3. At D21 (17 days of rest after 4 days stimulation), cells are harvested and phenotyped for CD4, CD27, CD127, CD45RO, and CCR7 surface expression.

Protocol for Isolating Mononuclear Cells from Bone Marrow (Control Cell Source)
1. Obtain de-identified bone marrow samples from a commercial vendor or local resource. BM aspirates should be from healthy volunteers, ideally between the ages of 18-35 years old.
2. Perform all steps at room temperature. Perform all steps that require direct access to the aspirate inside a BSC.
3. Transfer 20 mL of bone marrow to a 50 mL Falcon tube
4. Add 30 mL of PBS and pipette sample thoroughly to remove any lumps. (PBS 1× w/o Ca, w/o Mg (CCF Media Lab 121-1000p, Lot#262))
5. Pass through a 70 um cell strainer
6. Press pipette tip against membrane of strainer to help sample pass through
7. Wash the 50 mL Falcon tube with 50 mL PBS and run this rinse through another strainer.
8. This yields a bone marrow to PBS ratio of 1:3
9. Pipet 15 mL of Ficoll-Paque density gradient medium into a 50 mL Sepmate Tube. Place the pipet tip against the vertex near the bottom of the tube. Slowly fill bottom of tube, make sure no bubbles are present. (Ge Healthcare 17-1440-03 Lot #10241256).
10. Very slowly pipet 25 mL of the diluted blood-PBS mixture into the 50 mL Sepmate tube that contains the Ficoll. Place the pipette tip against the side of the tube and slowly release the mixture into the tube, making sure that no blood enters the bottom portion of the sepmate tube.
11. Keep Sepmate tube vertical
12. Centrifuge (at 2,400 rpm (1,200×g) for 40 minutes with the brake on (Acceleration program 9 and deceleration Program 6) [ThermoFisher Sorvall Legend XTR]
13. After centrifugation (RBCs remain on the bottom) the top layer is pipetted off. The top layer contains the buffy coat, along with the plasma. Combine this fraction with layers from other tubes into a 50 mL falcon tube.
14. Add PBS to make volume up to 50 mL and gently resuspend cells. Centrifuge these cell suspensions at 1,200 rpm for 8 minutes.
15. Aspirate supernatant leaving the pellet at the bottom of the tube. Gently tap the tube to loosen the pellet and add up to 50 mL PBS to resuspend
16. Centrifuge cell suspensions at 1,200 rpm for 8 minutes
17. Aspirate supernatant and repeat the two above steps ("Aspirate supernatant leaving the pellet", "centrifuge cell suspensions")
18. Aspirate supernatant. At this time the cell pellet should be white/translucent. If so, proceed to the step "suspend cell pellet with 10 mL of IMDM" below. If the pellet is reddish or there is a red subpellet, proceed with the next step.
19. Depending on nucleated red blood cell concentration, use ACK lysing buffer to lyse RBC. Pipet 4 mL of buffer to suspend the pellet. After 4 minutes, spin down the tubes at 1,200 rpm for 8 minutes. (Ack Lysing Buffer (Gibco A10492-01))
20. Aspirate supernatant and wash cells with 1×PBS as per the "Aspirate supernatant leaving the pellet" and "centrifuge cell suspensions" steps above
21. Suspend cell pellet with 10 mL of IMDM with 20% Human Serum and count cells. (IMDM w/glucose (12440053 GIBCO Lot#1812207); Human Serum (Gemini Bioproducts 100-512 Lot#H13ROOH)).
22. Take 10 µl of this suspension and add it to an Eppendorf. Add 90 µl of IMDM to the tube. Finally, add 100 µl of Trypan Blue stain to the same tube. All 10 µl of this mixture to hemocytometer, count cells, and calculate cell concentration and total cell numbers from resulting cell preparation.
23. After calculating cell number: plate cells at a density of 1.5×10^7 cells in a 75 cm^2 flask; with 15 mL of medium.
24. After 72-120 hours (3-5 days) add 10 mL fresh media to the flask
25. After 5-7 days remove media and non-adherent cells and add 25 mL fresh media
26. Examine cultures under a light microscope every day for evidence of cell adherence and growth.
27. Once cultures reach 90% confluence, passage the cells via dissociation buffer.
28. Expand cultures by passaging twice
29. After the second passage, at confluency, harvest the adherent cells and cryopreserve in aliquots of 1 million cells per vial for later use.

Results

FIG. 1 shows naïve $CD4^+$ T cell enrichment from umbilical cord blood.

Naïve $CD4^+$ T cells were purified from umbilical cord blood using density gradient separation (Ficoll) and magnetic cell isolation and separation (MACS).

Figure 2:
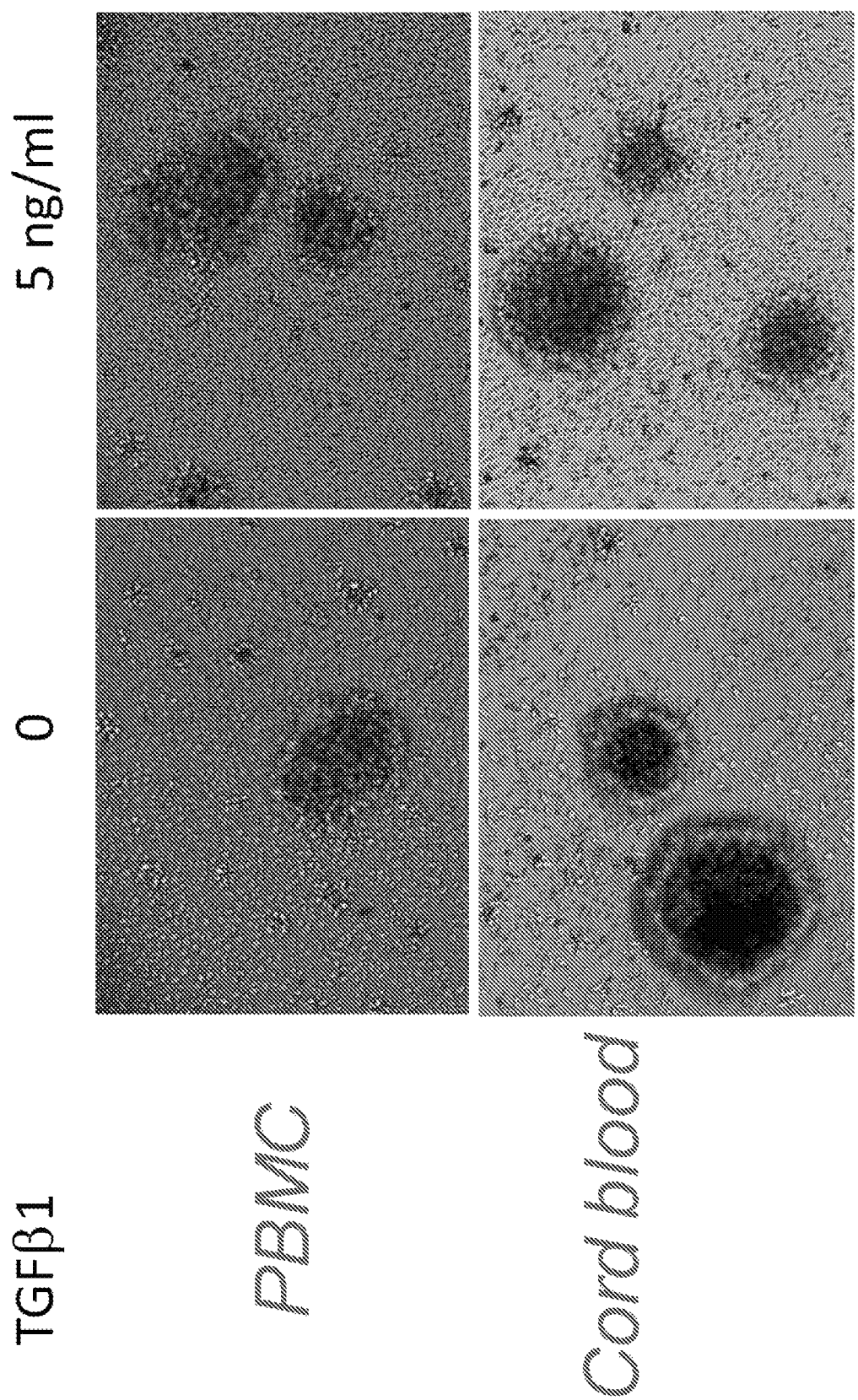
FIG. 2 shows that naïve CD4+ T cells from umbilical cord blood (UCB) and naïve CD4+ T cells from peripheral blood mononuclear cells (PBMCs) have similar activation responses. CD4+ T cells were activated using anti-CD2/3/28 stimulation in the presence of TGFβ1.

FIG. 2 shows that naïve $CD4^+$ T cells from umbilical cord blood (UCB) and naïve $CD4^+$ T cells from peripheral blood mononuclear cells (PBMCs) have similar activation responses. $CD4^+$ T cells were activated using anti-CD2/3/28 stimulation in the presence of TGFβ1. FIG. 2 shows cells at day four of stimulation.

Figure 3:
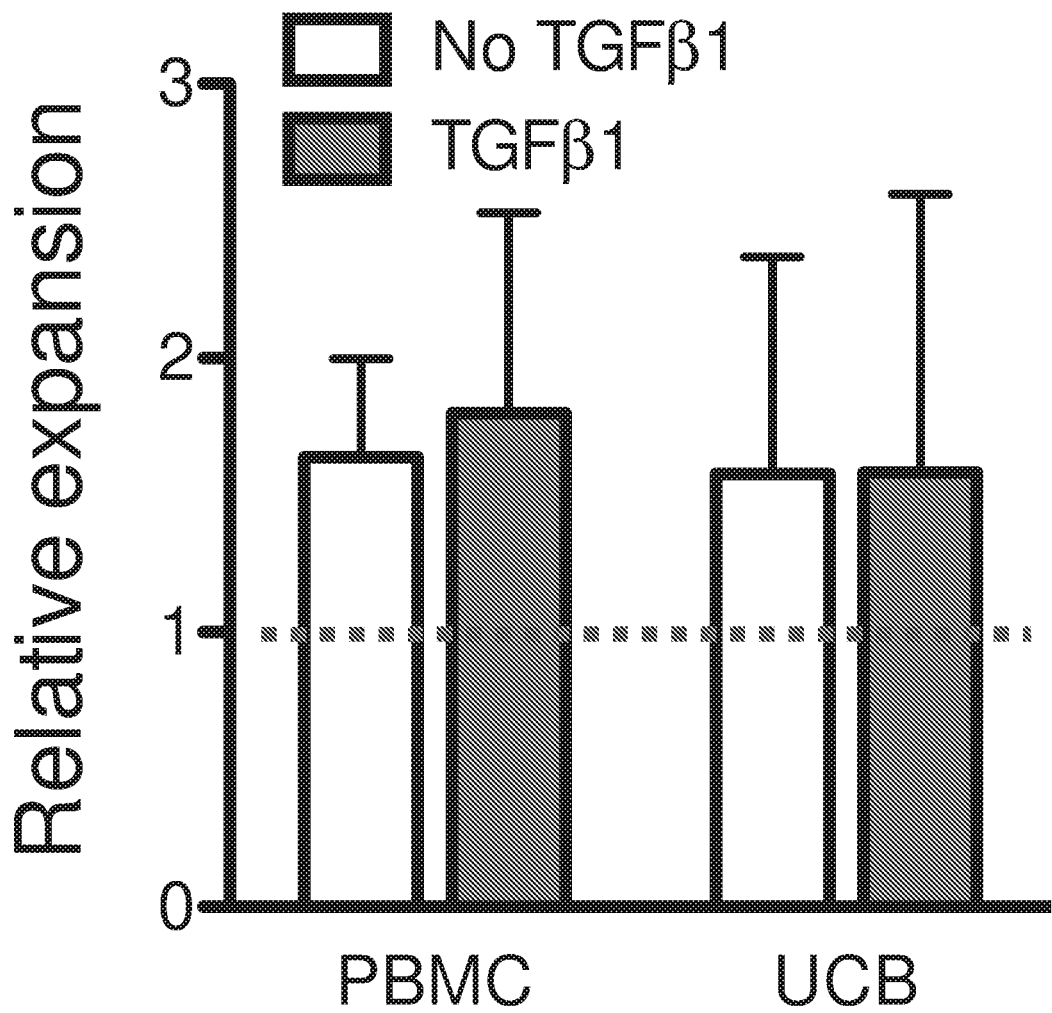
FIG. 3 shows that UCB and PBMC derived iTregs have similar relative expansion.

FIG. 3 shows that UCB and PBMC derived iTregs have similar relative expansion. FIG. 3 shows relative expansion between day zero and day four of anti-CD2/3/28 stimulation in the presence of TGFβ1.

Figure 4:
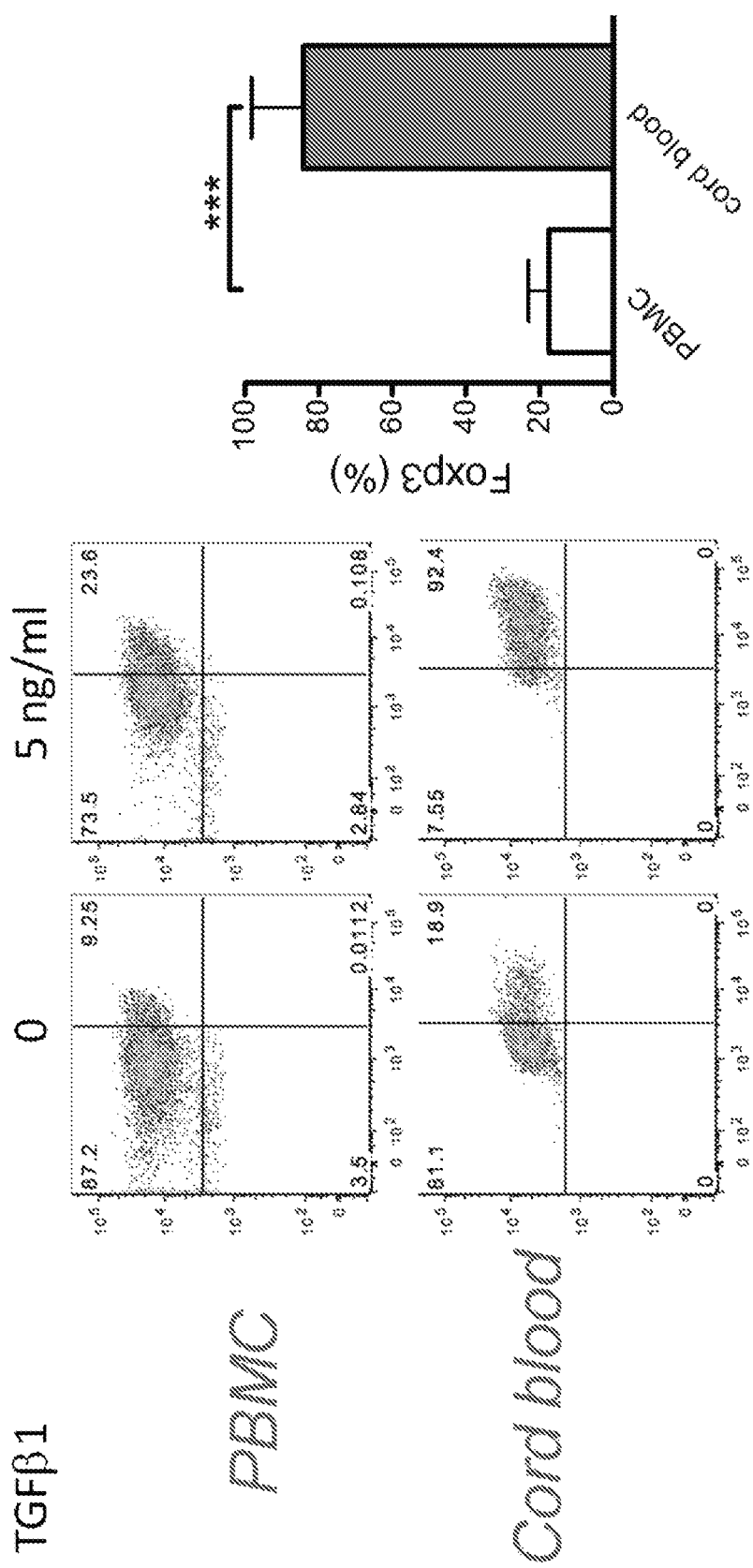
FIG. 4 shows that UCB CD4+ T cells yield higher Foxp3+ iTregs than PBMC CD4+ T cells.

FIG. 4 shows that UCB $CD4^+$ T cells yield higher $Foxp3^+$ iTregs than PBMC $CD4^+$ T cells.

Figure 5:
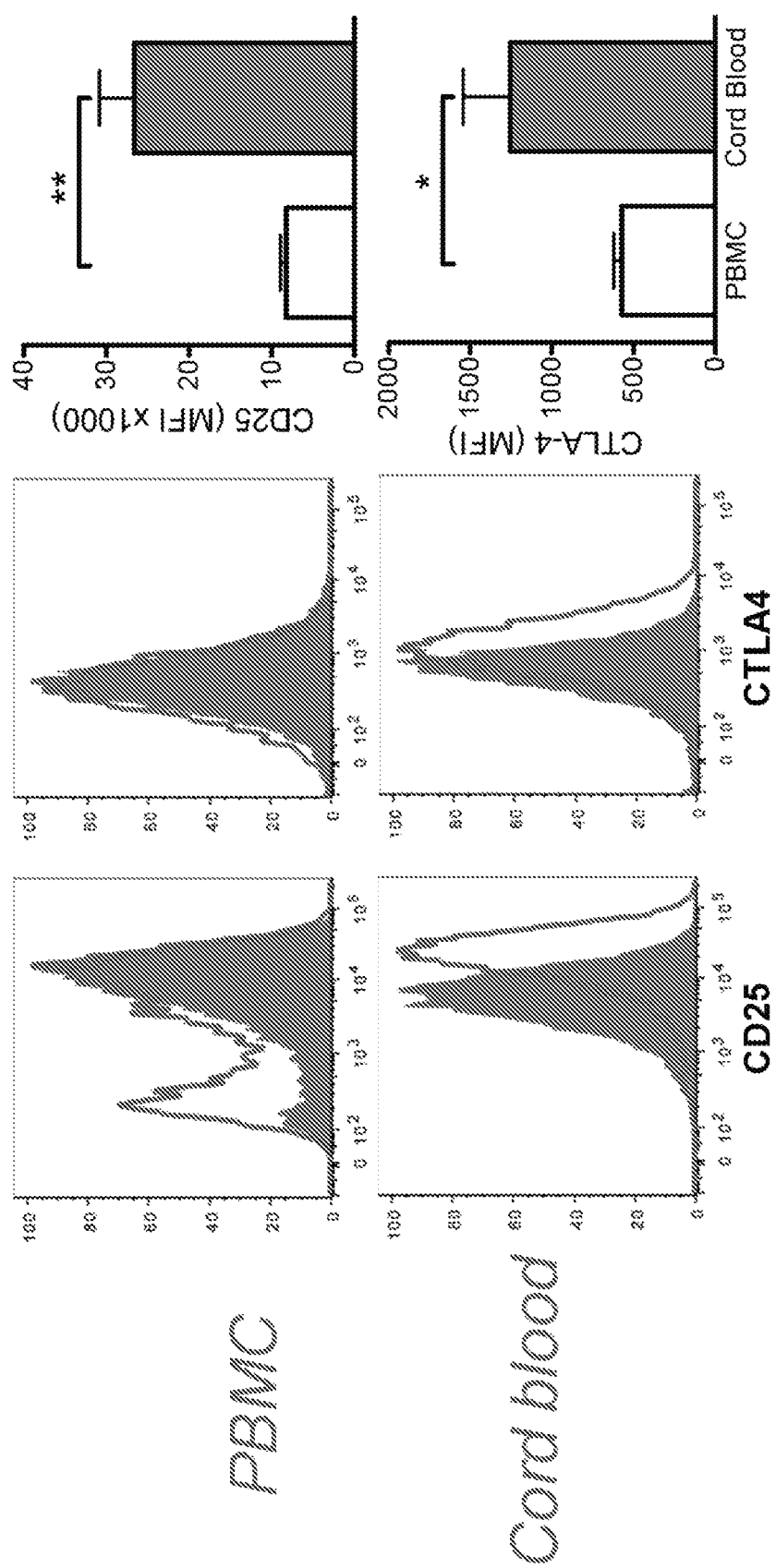
FIG. 5 shows that UCB derived iTregs have higher CD25/CTLA-4 expression than PBMC derived iTregs. The solid graph is control. The hollow line graph is iTreg.

FIG. 5 shows that UCB derived iTregs have higher CD25/CTLA-4 expression than PBMC derived iTregs. The solid graph is control. The hollow line graph is iTreg.

Figures 6A, 6B:
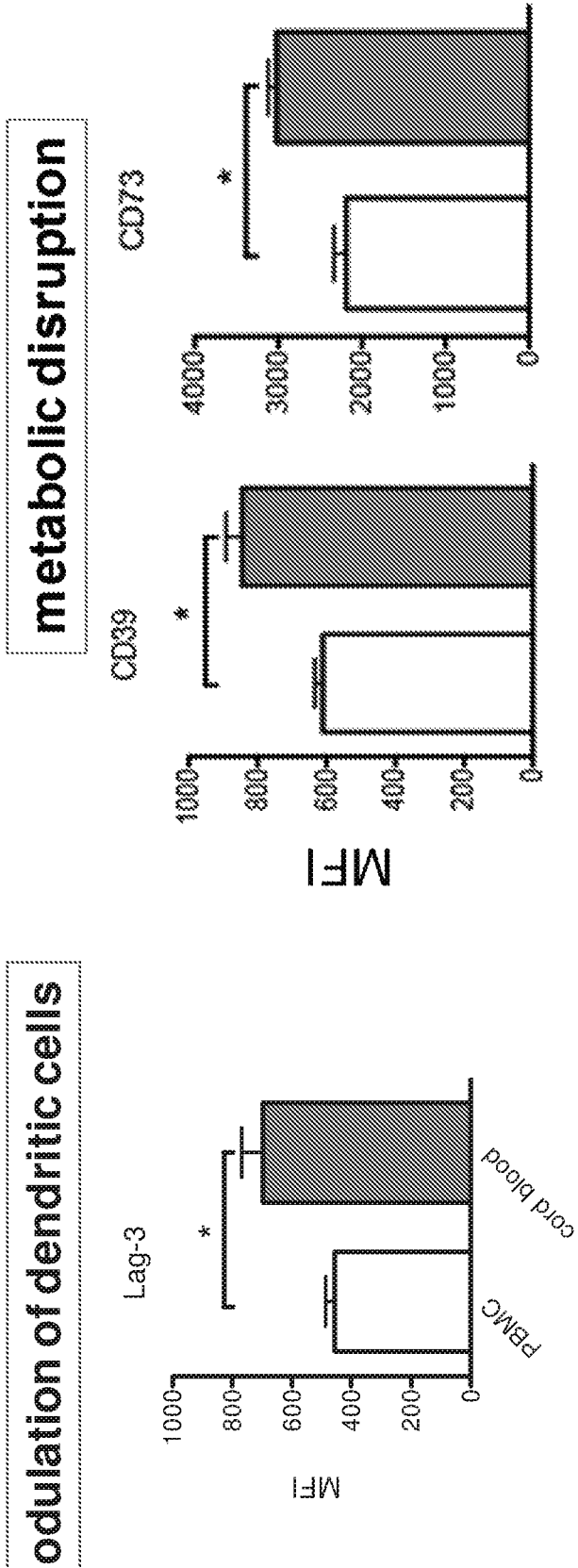
FIGS. 6A-6B show that UCB derived iTregs have higher expression of immune regulatory molecules relative to PBMC derived iTregs.

FIGS. 6A-6B show that UCB derived iTregs have higher expression of immune regulatory molecules relative to PBMC derived iTregs. FIG. 6A shows that UCB derived iTregs have higher modulation of dendritic cells relative to PBMC derived iTregs. FIG. 6B shows that UCB derived iTregs have higher metabolic disruption relative to PBMC derived iTregs.

Figure 7:
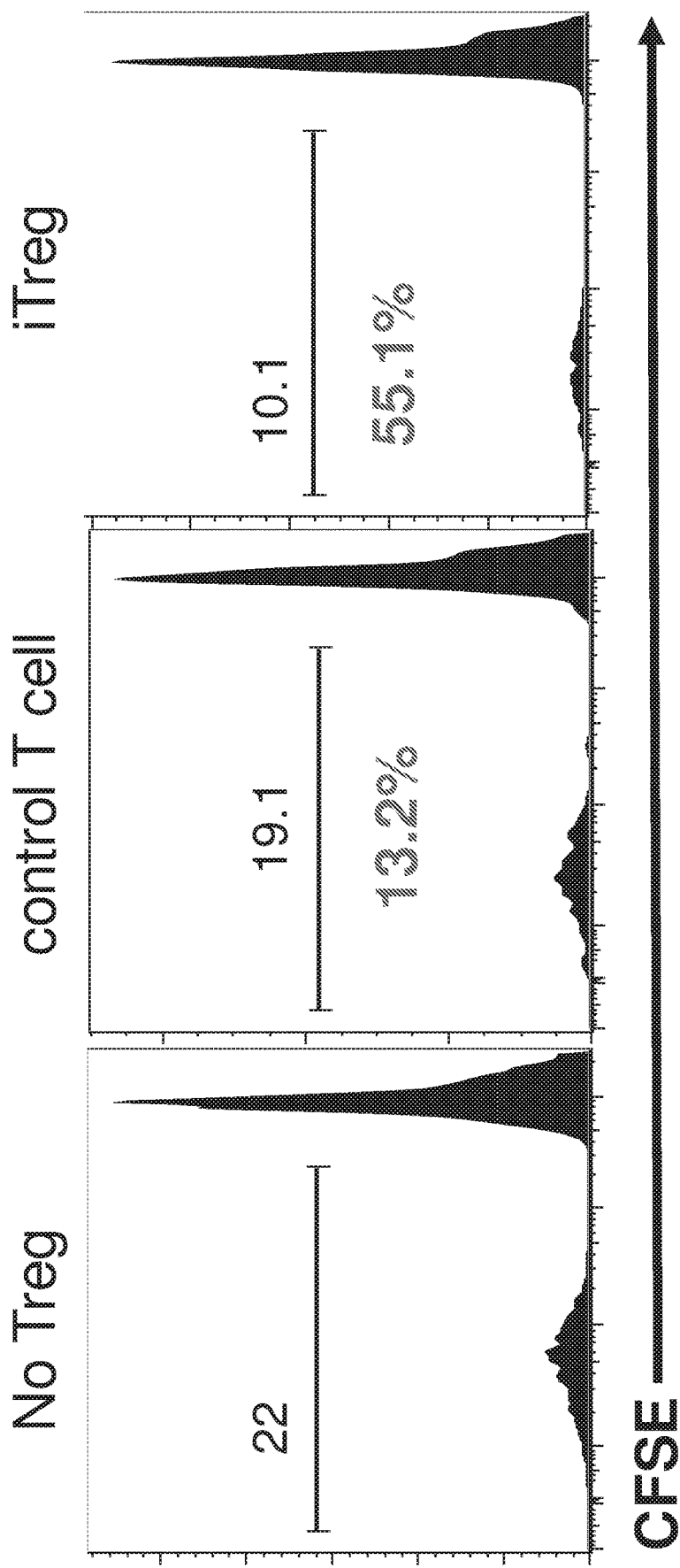
FIG. 7 shows robust T cell suppression by UCB derived iTregs. Responder CD4+ T cell proliferation against allo-antigen was measured. Responder: (A) CFSE labeled healthy donor naïve CD4+ $1\times10^5$. Allo-antigen: (B) healthy donor T cell depleted PBMC irradiated $1\times10^5$.

FIG. 7 shows robust T cell suppression by UCB derived iTregs. Responder $CD4^+$ T cell proliferation against allo-antigen was measured. Responder: (A) CFSE labeled healthy donor naïve $CD4^+$ $1 \times 10^5$. Allo-antigen: (B) healthy donor T cell depleted PBMC irradiated $1 \times 10^5$.

Figure 8:
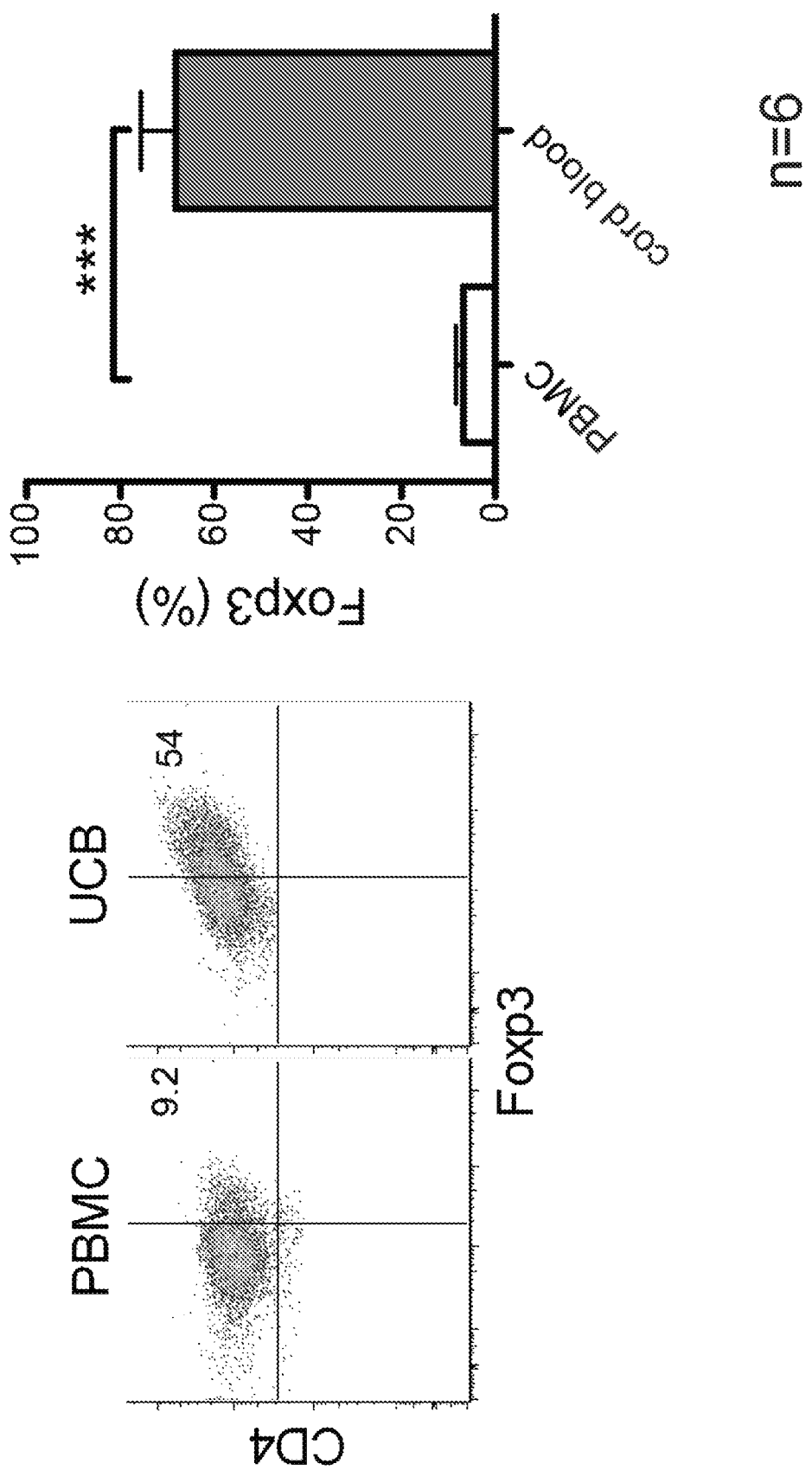
FIG. 8 shows that UCB derived iTregs have higher stability of Foxp3+ after resting relative to PBMC derived iTregs. Resting: $5\times10^5$ cells were stimulated 4 days and rested 48 hrs with IL-2 in the fresh media.

FIG. 8 shows that UCB derived iTregs have higher stability of $Foxp3^+$ after resting relative to PBMC derived iTregs. Resting: $5 \times 10^5$ cells were stimulated 4 days and rested 48 hrs with IL-2 in the fresh media.

Figure 9:
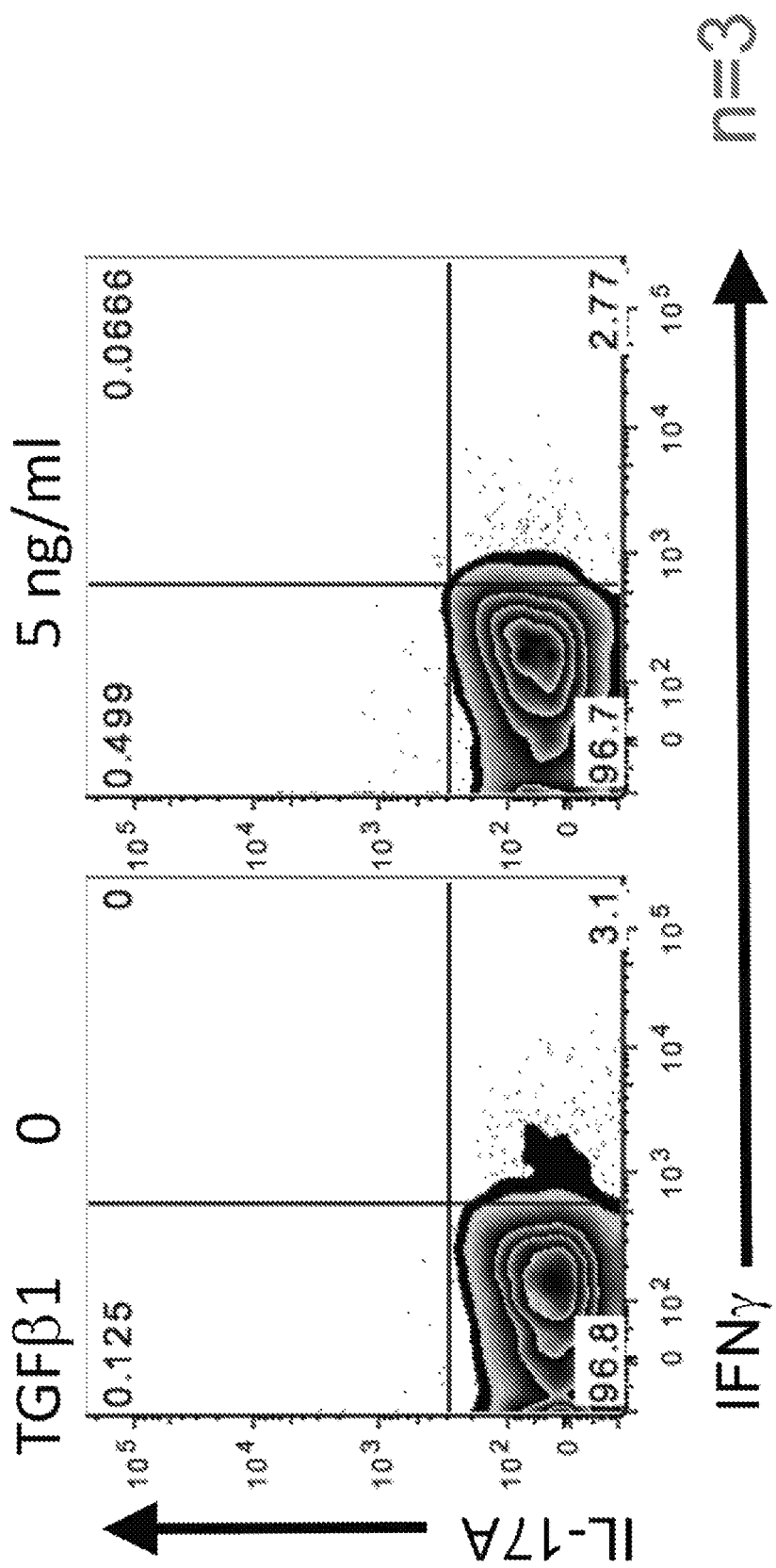
FIG. 9 shows that UCB iTreg generation does not lead to outgrowth of inflammatory CD4+ T cells as no inflammatory CD4+ T cells were detected.

FIG. 9 shows that UCB iTreg generation does not lead to outgrowth of inflammatory $CD4^+$ T cells as no inflammatory $CD4^+$ T cells were detected.

Figure 10:
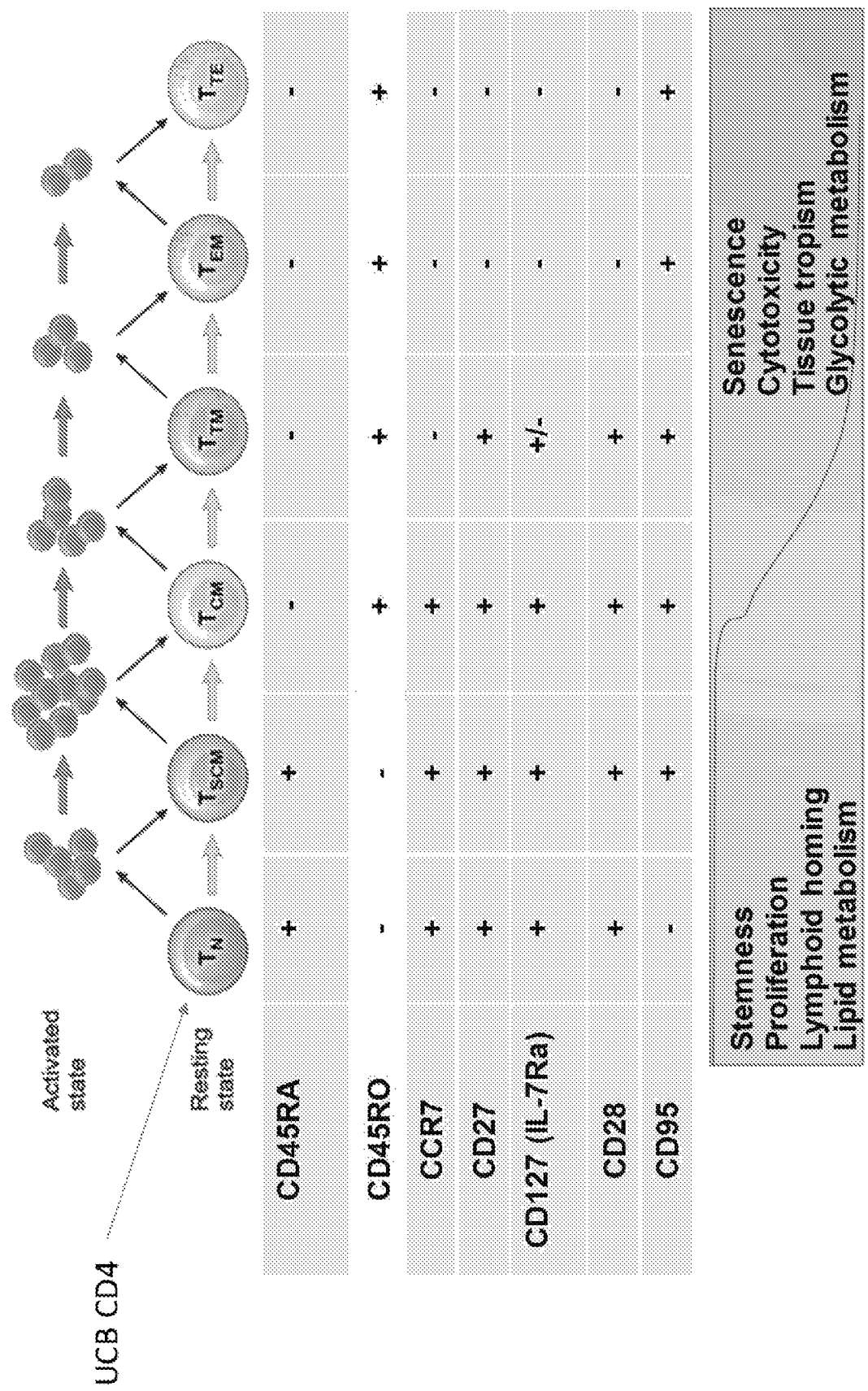
FIG. 10 shows T-cell characteristics throughout differentiation. Naïve CD4+ T cells from UCB are at the $T_N$ resting state.

FIG. 10 shows T-cell characteristics throughout differentiation. Naïve $CD4^+$ T cells from UCB are at the $T_N$ resting state.

Figure 11:
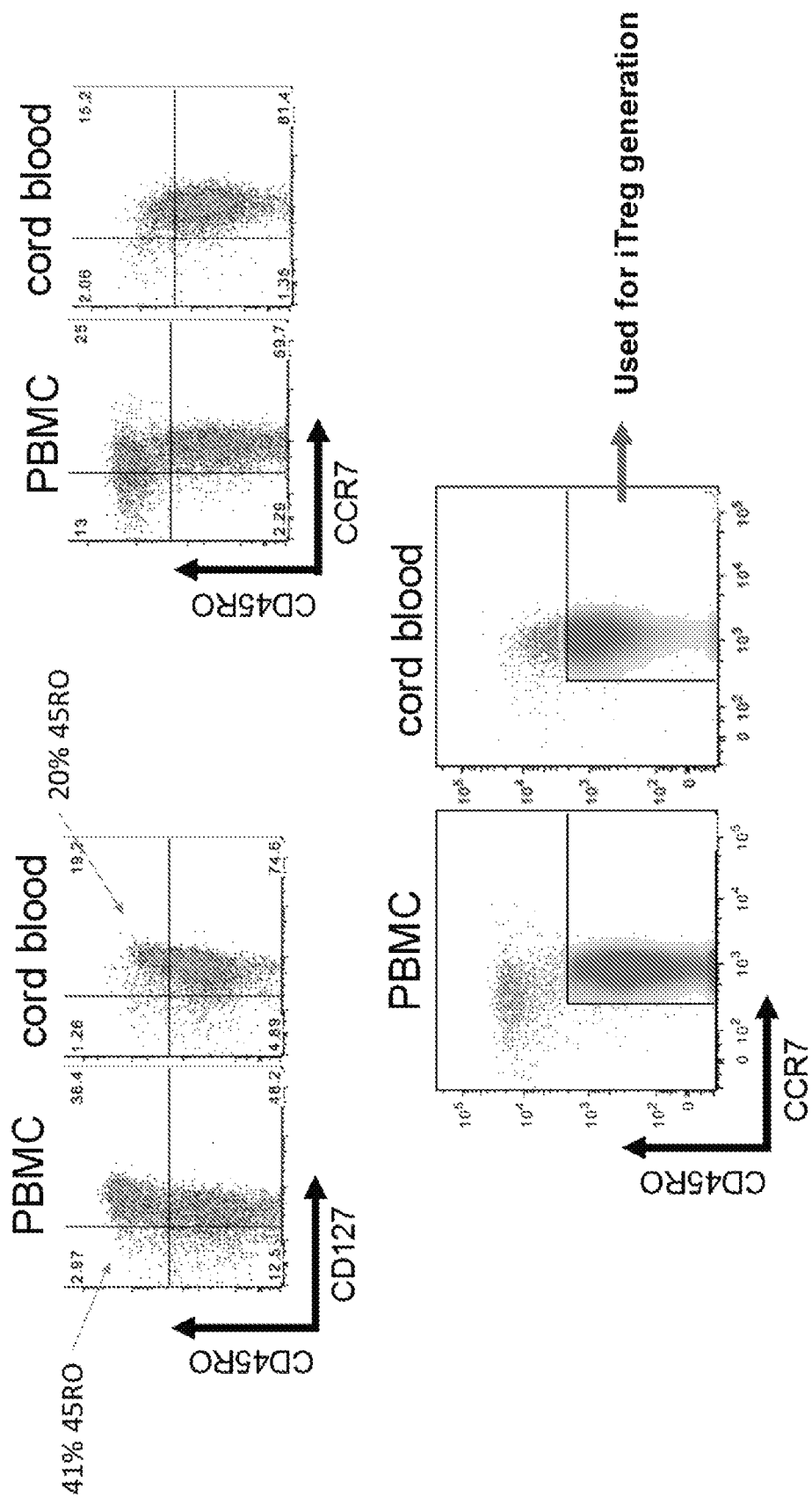
FIG. 11 shows a comparison of phenotypes between CD4+ T cells from UCB and CD4+ T cells from PBMCs.

FIG. 11 shows a comparison of phenotypes between $CD4^+$ T cells from UCB and $CD4^+$ T cells from PBMCs.

Figure 12:
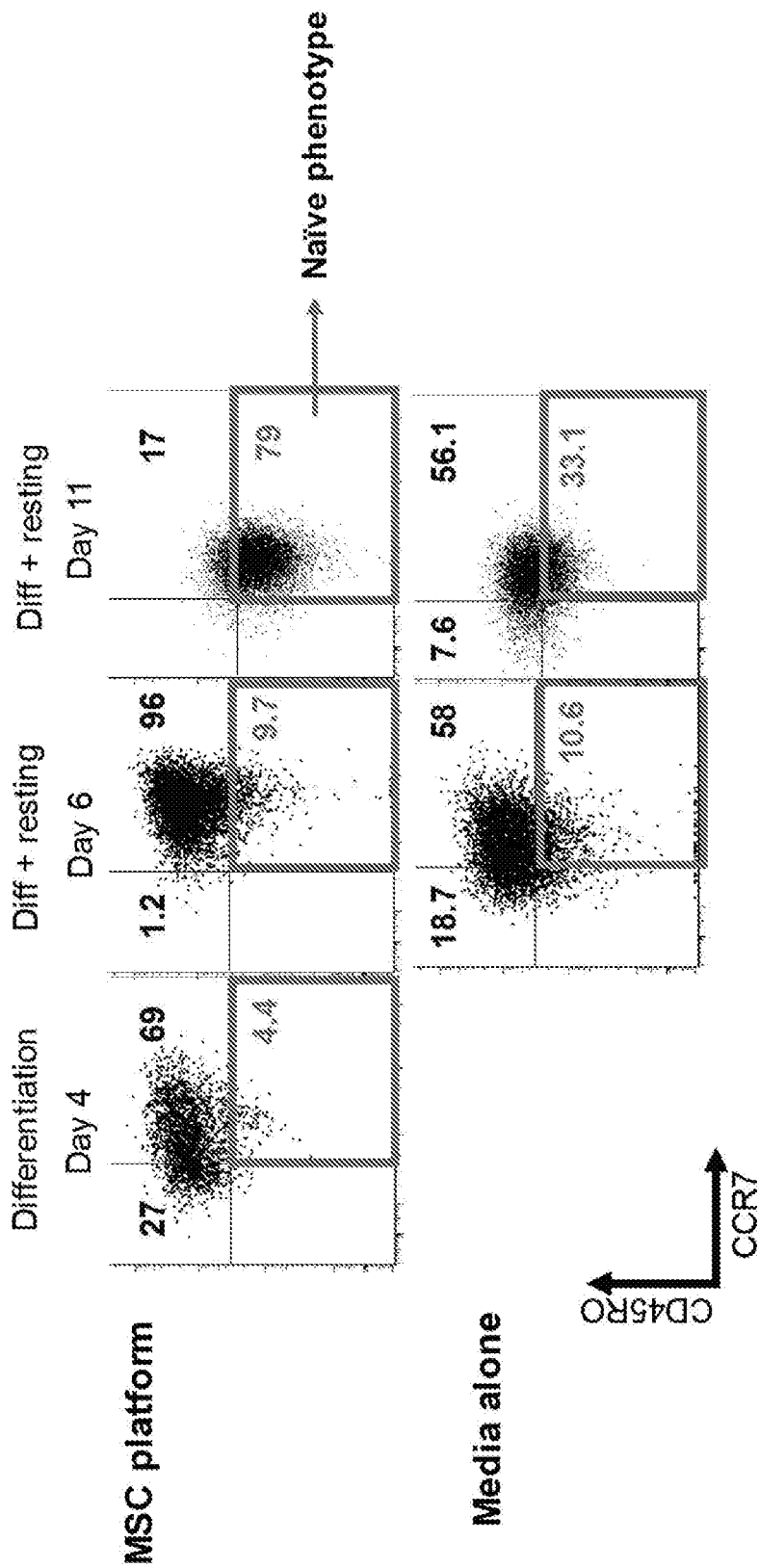
FIG. 12 shows that a mesenchymal stromal cell platform maintains naïve phenotype of UCB derived iTregs. CCR7 expression is included here given its known requirement for the in vivo function of CD4+ CD25+ regulatory T cells.

FIG. 12 shows that a mesenchymal stromal cell platform maintains naïve phenotype of UCB derived iTregs. CCR7 expression is included here given its known requirement for the in vivo function of CD4+ CD25+ regulatory T cells.

Higher Expression of BACH2 and Higher Number of Foxp3+ iTreg Generated from UCB Naive CD4+ T Cells.

Figures 13A, 13B, 13C:
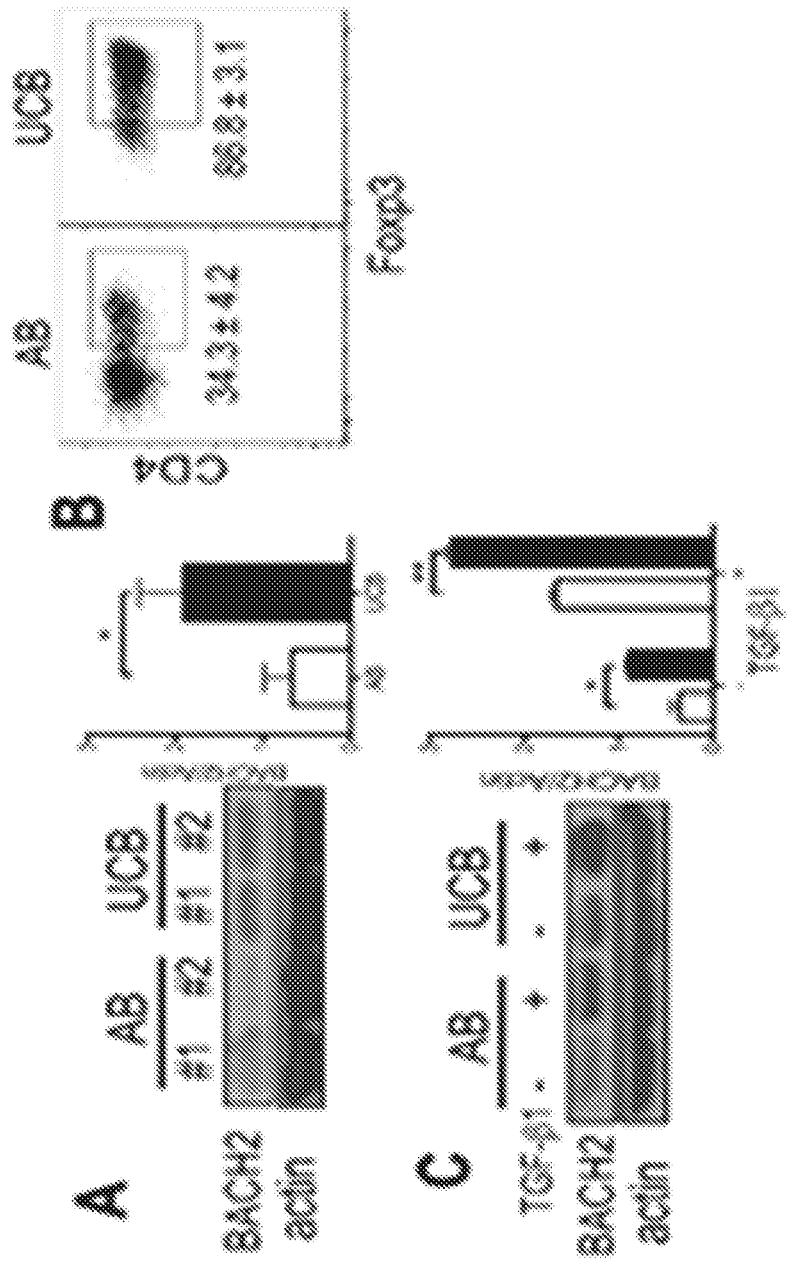
FIGS. 13A-13C show higher expression of BACH2 and higher number of Foxp3+ iTreg generated from UCB naive CD4+ T cells. Bach2 expression in adult peripheral blood and umbilical cord blood naïve CD4T cells.

To measure BACH2 expression on naïve CD4+ T cells, human UCB and AB were collected and mononuclear cells (MNCs) were purified using a density gradient followed by CD45RO– CD4+ selection of T cells using the Miltenyi autoMACs system (Auburn, CA) (21). Applicants previously reported that levels of BACH2 protein were significantly elevated from UCB naïve CD4+ T cells and here also observe that Bach2 expression also is highly increased in UCB iTreg. Cell lysates were collected from unstimulated and stimulated adult or UCB CD4+ T cells using radio immune precipitation assay (RIPA) buffer and quantitated using BCA assay (BioRad, CA). Concentrations of total protein from 50 ug were separated on 10% SDS-PAGE, transferred to a PVDF membrane (Millipore, CA). Expression of Bach2 protein was increased in unstimulated UCB naïve CD4 T cells (FIG. 13A). Next measured Foxp3 expression on CD4+ T cells in AB and UCB CD4+ T cells was measured. MACS purified naïve CD4+ T cells were stimulated with anti-CD2/CD3/CD28 mAb coated dynabeads for 4 days with 5 ng/ml TGFβ1 at 5×105 cells and subsequently tested for Foxp3 expression. UCB CD4+ T cells expressed significantly enhanced Foxp3 protein compared to AB CD4+ T cells (FIG. 13B). Also, after differentiation into Foxp3+ iTregs BACH2 expression was still highly maintained in UCB CD4+ T cells (FIG. 13C). These data suggest that UCB CD4+ T cells highly express BACH2 protein in steady stage conditions and after differentiation into Foxp3+ iTreg.

BACH2 Gene Silencing by shRNA Transfection Down Regulated Foxp3 Expression.

Figures 14A, 14B:
FIGS. 14A-14B show knock-down of BACH2 with shRNA in UCB naïve CD4 T cells results in decreased conversion into Foxp3* iTreg cells.

Based on the finding that BACH2 protein levels increased in UCB naïve CD4+ and iTregs, BACH2 was tested as an essential factor for differentiation of UCB naïve CD4+ T cells into Foxp3+ iTreg. UCB naïve CD4+ T cells were isolated as stated above. UCB CD4+ T cells were transiently transfected with shRNA targeting BACH2 mRNA (Dharmacon, CO) along with appropriate controls (empty vector) followed by primary stimulation with anti-CD2/CD3/CD28 mAb coated dynabeads. BACH2 shRNA treated UCB CD4+ T cells and control shRNA treated UCB CD4+ T cells were cultured in TGFβ1 added media supplemented with 10% AB and harvested at 4 days after transfected to measure BACH2 protein expression. Treating UCB CD4+ T cells with BACH2 shRNA resulted in a BACH2 protein decrease (~50%) compared to control shRNA treated UCB CD4+ T cells (FIG. 14A). BACH2 knock-down in human UCB CD4+ T cells diminishes Foxp3+ T cells compared to control shRNA treated CD4+ T cells (FIG. 14B). These results suggest that BACH2 may serve as a partner transcription factor regulating of Foxp3+ expression in UCB-derived iTregs.

UCB iTregs Exhibit Enhanced Suppressive Effects Compared to AB iTreg In Vitro.

Figures 15A, 15B:
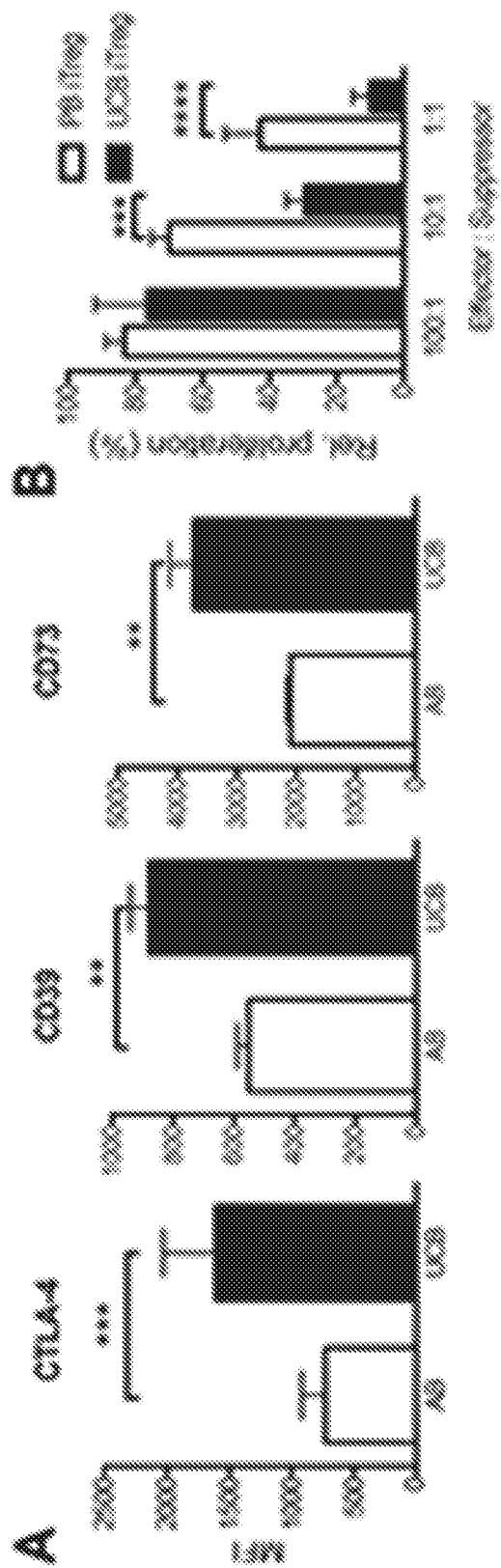
FIGS. 15A-15B show phenotype and suppressive functions of UCB iTreg.

As UCB-derived iTregs express more robust and sustained FoxP3 expression, UCB iTreg was compared to AB iTreg suppressive function. AB and UCB iTregs were generated in identical conditions as stated above. As shown in FIGS. 15A-15B, UCB iTregs expressed significantly enhanced CTLA-4 and CD39/CD73 inhibitory molecules (FIG. 15A) as well as suppressive activity (FIG. 15B). These results demonstrate that UCB iTregs exhibit significantly enhanced suppressive function compared to AB iTregs.

BM MSC Platform Maintains Tregs Foxp3 Stability and Suppressive Effect In Vitro.

Figures 16A, 16B, 16C, 16D:
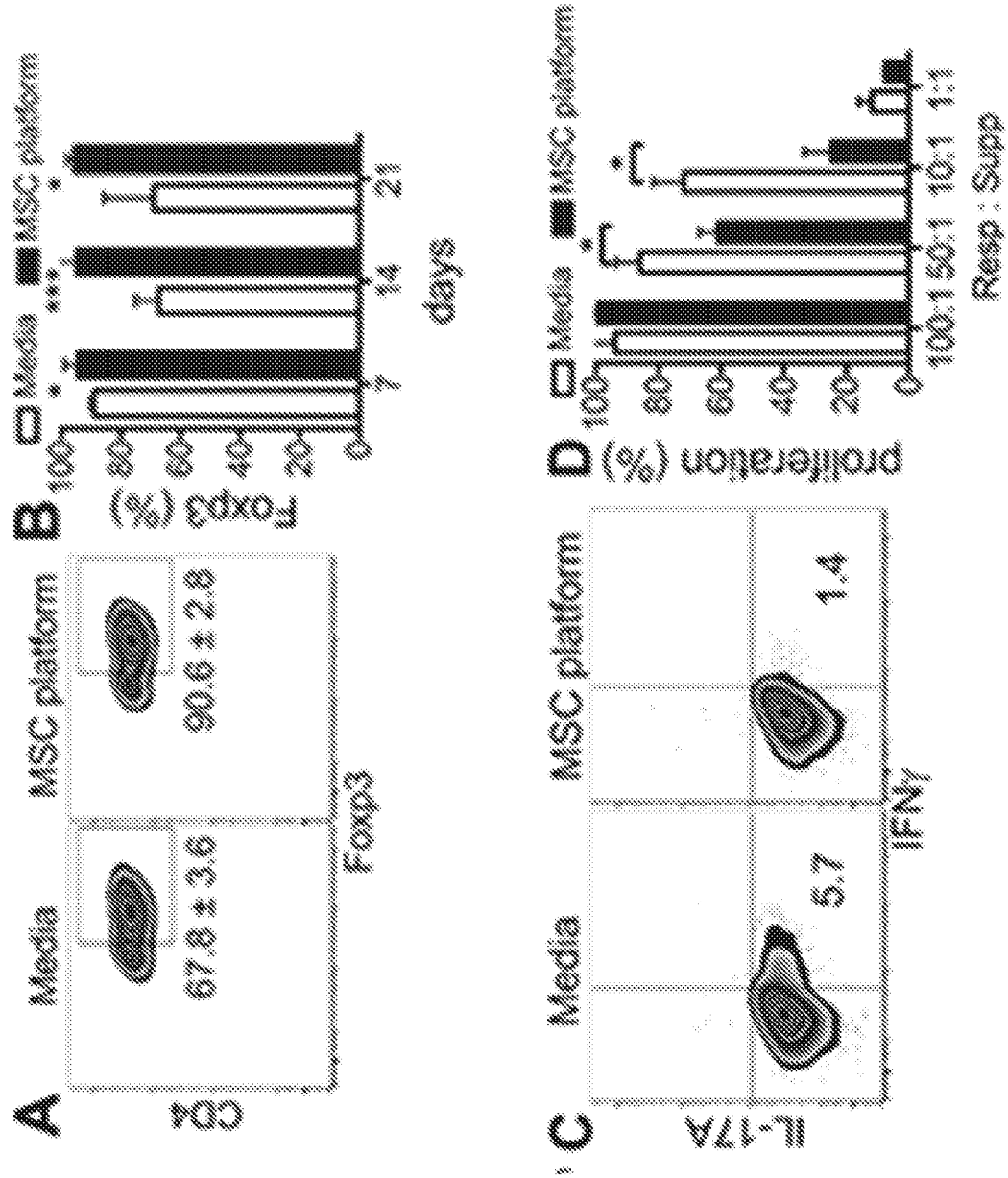
FIGS. 16A-16D show that a MSC platform enhances Foxp3 stability and suppressive function of UCB iTreg cells.

To test the role of MSC platform in UCB iTreg suppressive function and Foxp3 stability, a human MSC feeder layer was utilized during iTreg in vitro expansion. UCB iTregs were harvested 4 days after differentiation from naïve CD4 T cells. Next iTregs were expanded for 21 days in standard conditions in media vs. MSC platform conditions with 100 U/ml recombinant IL-2 in 10% human AB X-VIVO15 media. UCB iTregs culture expanded over a MSC platform demonstrated robust sustained Foxp3 expression compared to UCB iTregs expanded in media condition alone (FIG. 16A). The effect of Foxp3 stability in UCB iTregs was maintained during 21 day culture expansion over a MSC platform (FIG. 16B). UCB iTregs expanded over an MSC platform did not demonstrate outgrowth of pro-inflammatory IFNγ nor IL-17A cytokine-producing cells (FIG. 16C). Moreover, it was observed that suppressive function of UCB iTregs expanded over an MSC platform was enhanced compared to UCB iTregs expanded in standard media condition (FIG. 16D). These results demonstrate that an MSC platform condition confers in UCB iTregs significantly improved Foxp3 stability and suppressive function during prolonged ex vivo expansion.

CONCLUSIONS

Foxp3$^+$ expressing CD4+ iTreg cells were increased in TGF-β1 added condition.

Relative CD4$^+$ iTreg cell expansion was similar between 0 and 5 ng/ml TGF-β1 added condition.

During resting/expansion phase, iTregs maintained naïve phenotype of CD4$^+$ T cells when cultured over seeded bone marrow derived MSC.

iTregs derived from UCB using the presently disclosed methods of derivation demonstrate greater Foxp3$^+$ expression compared to adult PBMCs (Foxp3$^+$ is a critical transcription factor in Treg essential for their function)

iTregs derived from UCB using the presently disclosed methods of ex vivo selection and stimulation demonstrates greater stability of Foxp3$^+$ expression compared to adult PBMC CD4 T cells from UCB used to generate iTregs demonstrate a naïve phenotype with high expression of CD45RA compared to adult PBMC.

iTregs derived from UCB using the presently disclosed methods have higher expression of CD25 and CTLA4 that are critical to the suppressive function of iTreg compared to adult PBMC.

iTregs derived from UCB using the presently disclosed methods have higher expression of Lag-3 essential to Treg function to modulate antigen presenting cells.

iTregs derived from UCB using the presently disclosed methods have higher expression of CD39 and CD73 indicative of metabolic function of Treg essential to their suppressive function.

iTregs derived from UCB using the presently disclosed methods have high suppressive capability in mixed lymphocyte culture.

iTregs derived from UCB using the presently disclosed methods do not demonstrate outgrowth of inflammatory CD4 T cells during ex vivo culture.

Bone marrow derived mesenchymal stromal cells maintain naïve phenotype of iTreg generated from UCB CD4 T cells during ex vivo culture.

iTreg cultures over bone marrow derived MSC do not express T cell exhaustion surface markers compared with that observed in standard suspension cultures.

Example 2: Regulation of FOXP3 in Induced T Regulatory Cells Derived from Human Umbilical Cord Blood Vs. Adult Peripheral Blood Methods
Human UCB and Adult Peripheral Blood Samples.

Acquisition of de-identified volunteer young adult peripheral blood and UCB were obtained. Mononuclear cells were isolated by Ficoll-Paque PLUS (GE Healthcare Life Sciences, Piscataway, NJ) density gradient centrifugation with SepMate-50 tubes (STEMCELL Technologies, Vancouver, BC, Canada).

Naive CD4 Isolation and iTreg Generation.

Naïve CD4$^+$ T-cells were isolated by Miltenyi auto MACS (Auburn, CA, USA) with sequential CD45RO$^{neg}$ and CD4$^+$ selection per manufacturer's instructions. The purity of selected UCB and adult PB naïve CD4$^+$ T-cells was assessed by multi-parameter flow cytometry and exceeded 97%. The isolated naïve CD4$^+$ T cells were activated in vitro with CD2/3/28 monoclonal antibody coated dynabeads (beads to cell ratio, 1:2; Miltenyi) with added IL-2 (100 U/ml, Miltenyi) with or without 5 ng/ml transforming growth factor-β (TGF-β; Peprotech, Rocky Hill, NJ) in 48-well culture plates at $5\times10^5$ cells per well. The culture medium consisted of X-VIVO 15 (Lonza, Walkersville, MD) with 10% heat-inactivated human serum albumin (Gemini Bio-product, Sacramento, CA). The cells were stimulated 4 days, washed with PBS, and used for chromatin immunoprecipitation (ChIP), FOXP3/CTLA-4 qPCR and Western Blot, shRNA transfection, mixed lymphocyte culture, and FACS analysis. Expansion of FOXP3$^+$ iTregs was performed with CD25$^+$ cells MACS purified from day 4 TGFβ-induced AB and UCB iTreg. $0.5\times10^6$ purified cells were split with fresh media with 100 U/ml IL-2 added, and culture media was replaced every other day until clay 21.

Western Blot.

UCB and AB naïve CD4$^+$ T-cells and differentiated iTreg were lysed using radio-immune precipitation assay (RIPA) buffer[27] and protein was quantified using the Bradford assay (BioRad, Hercules, CA), with 40 μg of protein separated by 8% SDS-PAGE. Proteins were electro-transferred onto Immobilon™ membrane (Millipore) and were probed with polyclonal rabbit anti-BACH2 (ab83364) antibody, monoclonal rabbit anti-NFAT1 (EPR2973; ab92490) antibody (Abcam, Cambridge, MA), and monoclonal mouse/human/rat anti-β-actin antibody (R&D system, Minneapolis, MN). Applicable HRP-conjugated secondary antibodies were used with ECL™ chemi-luminescence to observe relevant bands using x-ray film.

FACS Analysis.

Cells were harvested day 4 of stimulation and surface stained with CD25, CD39, CD62L, CD73, CD223, CTLA-4, ICOS, PD-1, Tim-3, (BD Bioscience, San Diego, CA) and TIGIT (Biolegend, San Diego, CA). For FOXP3 staining, 3G3 PE (Miltenyi) or 259D/C7 PE (BD Pharmingen) anti-FOXP3 antibody was used. Stimulated cells were fixed after surface staining and permeabilized with Fixation/Permeabilization kit according to the manufacture's protocol (Miltenyi). Expanded cells were analyzed by FACS including CD62L and FOXP3 at day 7 and 21. A Fortessa instrument (BD Biosciences, San Diego, CA) was used for data acquisition and the data was analyzed using FlowJo software (Tree Star, Inc., Ashland, OR).

Quantitative RT-PCR.

Total RNA was extracted from the cells using GeneJet RNA Purification Kit (Thermo Scientific, Waltham, MA) and quantified. cDNA was subsequently synthesized using a SuperScript III reverse transcriptase (Invitrogen, Carlsbad, CA). Real time quantitative PCR was performed using gene specific primers and probe sets (Applied Biosystem, Foster City, CA) and an ABI 7500 PCR machine (Applied Biosystem). The qRT-PCR runs were performed in triplicate to quantify expression levels for each gene using Taq-man assays per manufacture instructions.

In Vitro Suppression Assay.

In vitro suppression assays were performed. Responder naïve CD4$^+$ T cells and Mitomycin C treated T cell depleted PBMC were prepared from a healthy donor. CFSE labeled naïve CD4$^+$ T cells were plated at a 1:1 ratio with mitomycin C treated T-depleted PBMC and varying concentrations of AB and UCB iTreg. Soluble anti-CD3 (2 μg/ml) (clone HIT3a, BD Bioscience) mAb was added. CFSE dilution was examined by flow analysis.

BACH2 shRNA Knockdown in Day 0 Naïve CD4 T Cells and Day 4 iTreg.

To address the potential role for BACH2 transcriptional regulation in UCB FOXP3$^+$ iTregs generation, BACH2 shRNA knockdown was performed after 16 h stimulation as described above. $5\times10^5$ UCB naïve CD4$^+$ T cells cultured for 4 days in iTreg induction conditions as described above to induce FOXP3$^+$ iTreg differentiation were transfected in the same conditions with GFP tagged empty or BACH2 shRNA virus by a spinoculation transduction method, GFP CD4$^+$ T cells FACS were sorted, and BACH2 expression measured by FACS. FACS sorted cells were used for appropriate experiments including measurement of FOXP3 and CTLA-4 expression by FACS and qPCR assay.

Identification of Putative Transcriptional BACH2 Binding Sites.

The 2.5 Kb sequence centered on the −1 exon of human FOXP3 was downloaded from NCBI at ncbi.nlm.nih.gov/sites/entrez. The sequence was analyzed for known putative transcription factor binding sites using Blast (Basic Local Alignment Search Tool) at blast.ncbi.nlm.nih.gov/Blast.cgi. The FOXP3 proximal promoter was examined for putative NFAT1 [NGGAAAHH] and AP-1 [TGAYTMMK] binding sites with particular attention to regions adjacent to the NFAT1 binding sites for partial AP-1 sites not scored by the algorithm. These regions were aligned manually and examined for similarity to the known consensus sequence for BACH2 [TGASTCAY]. Only those sequences with 2 or fewer mismatches exceeding 75% similarity to the BACH2 consensus site were considered further.

Cross-Linking Chromatin-Immunoprecipitation Assay (ChIP Assay).

ChIP assays were performed according to the cell signaling protocol (cellsignal.com/contents/resources/protocols/resources-protocols). UCB and AB naïve CD4$^+$45RA$^+$ T-cells were stimulated with TGF-β in conditions summarized above. After 4 days of stimulation cells were examined by ChIP. Between $1.0$-$1.5\times10^7$ cells were treated with 1% formaldehyde to cross-link protein to DNA. Protein-DNA lysates were mixed with 1:50 ratio of rabbit monoclonal BACH2 antibody (Cell Signaling, Boston, MA) then immune-precipitated with protein A/G Agarose Beads (D3T3G, Cell Signaling). After digestion of proteins by Proteinase K treatment, DNA was purified by DNA isolation spin column (Cell Signaling) and examined for the presence of the FOXP3 promoter by RT-PCR.

Luciferase Assay.

The human FOXP3 luciferase reporter (Luc) Jurkat recombinant cell line was used (BPS Bioscience, San Diego, CA). Cells were transfected by empty or BACH2 shRNA. After 16 h, cells were stimulated with CD2/3/28 monoclonal antibody coated dynabeads (beads to cell ratio, 1:2) with IL-2 (100 U/ml) with or without 5 ng/ml TGF-β in 96-well culture plates at $1\times10^4$ cells per well. Luciferase activities were measured after 24 h using the ONE-step™ luciferase assay system kit (BPS Bioscience).

Statistical Analysis.

Statistical comparative analyses were performed using the Student's t-test (Prism 6 software-GraphPad, La Jolla, CA). A p value of <0.05 was considered significant.

Results

Expression of BACH2 and NFAT1 in UCB Naïve CD4 and FOXP3$^+$ CD4 T Cells.

Figures 17A, 17B, 17C:
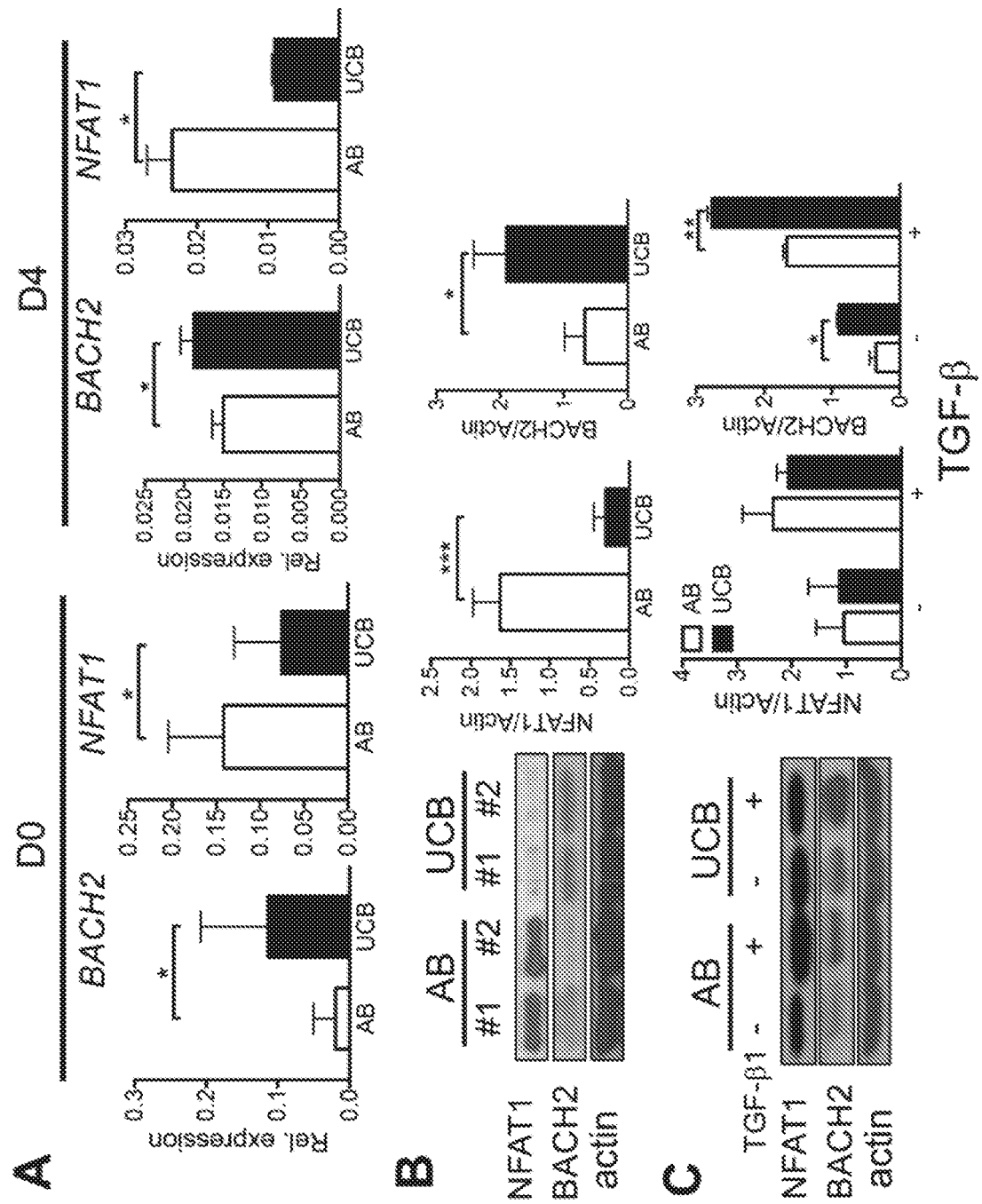
FIGS. 17A-17C show BACH2 and NFAT1 expression in AB and UCB naïve and TGF-β induced FOXP3+ CD4+ iTreg. (A) BACH2 and NFAT1 RNA expression by qRT-PCR of UCB and AB naive CD4+ CD45RA+ at baseline day 0 (D0) and Day 4 of AB and UCB FOXP3+ iTreg induction with CD2/3/28-stimulation, IL-2 100 U/ml, and TGF-β 5 ng/ml. Data are presented as relative mRNA expression (n=3-8). (B) BACH2 and NFAT1 protein expression in AB and UCB naïve CD4+ CD45RA+ T cells was measured by western blot analysis. (C) BACH2 and NFAT1 protein expression in day 4 TGF-β induced AB and UCB FOXP3+ iTreg was measured by western blot analysis. The image intensities for Western blots were normalized to β-actin. Images are representative of multiple western blots. Data are from multiple experiments (n=4-8). * $p<0.05$,  $p<0.01$, * $p<0.001$, unpaired Student t test.

Expression of BACH2 mRNA was significantly increased in UCB vs. AB naïve CD4$^+$45RA$^+$ T cells at baseline (day 0) and after 4 days (96 h) stimulation in iTreg differentiation conditions described above (FIG. 17A). NFAT mRNA expression was decreased in UCB naïve CD4+CD45RA+ at baseline and day 4 iTreg compared to AB (FIG. 17A). Protein levels of BACH2 in UCB naïve CD4+45RA+ T cells was higher than AB naïve T cells at baseline (day 0) and NFAT1 protein expression was lower in UCB naïve CD4+ CD45RA+ T cells vs. AB (FIG. 17B). On day 4 iTreg differentiation conditions (with or without TGF-β added), NFAT1 expression was similar in AB and UCB with however higher BACH2 expression measured in UCB CD4+ T-cells (FIG. 17C).

Absolute Number and FOXP3+ Expression in iTreg Derived from UCB vs. Ab Naïve CD4+ T Cells.

Figures 18A, 18B, 18C, 18D:
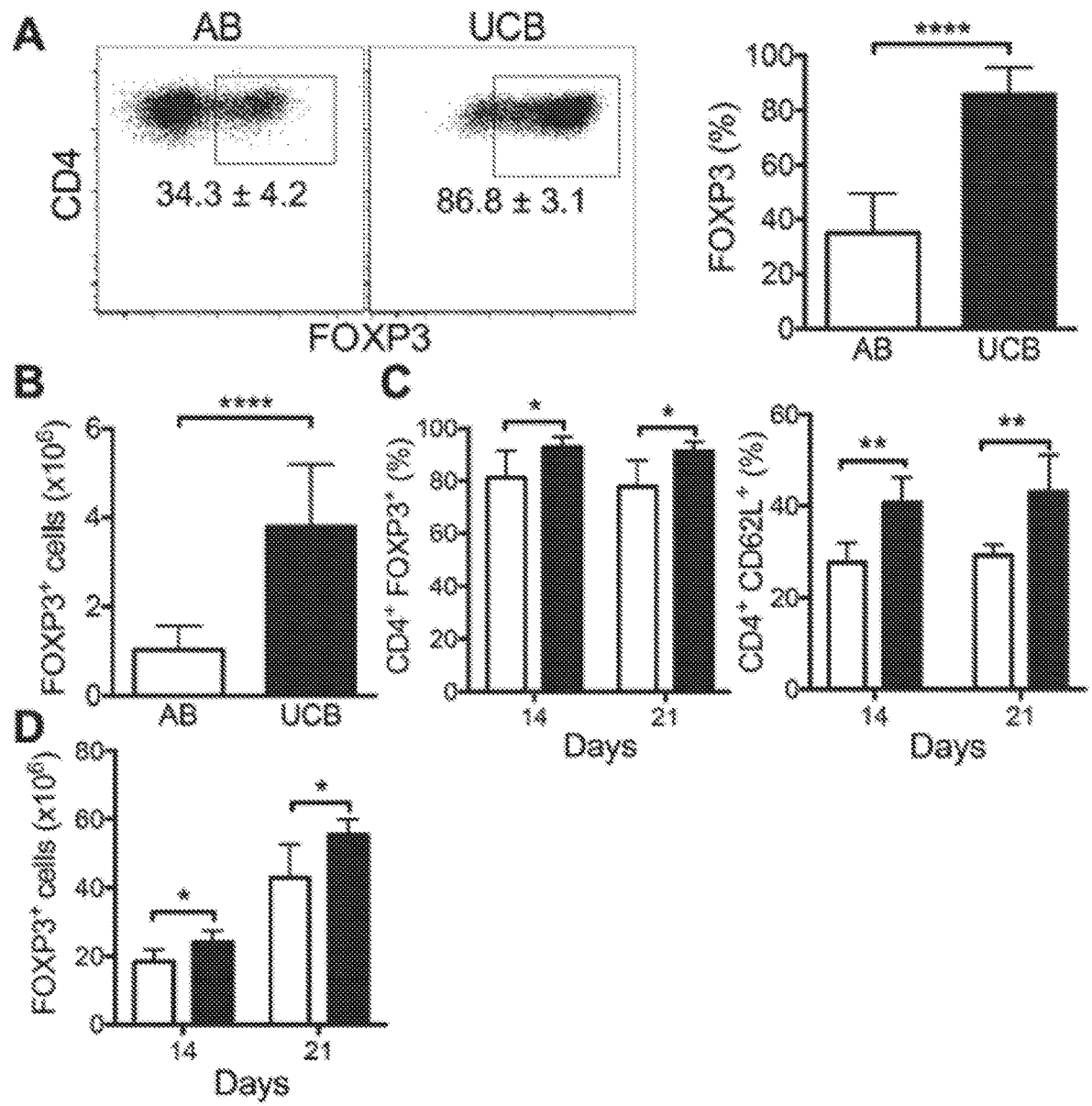
FIGS. 18A-18D show data from TGF-β induced FOXP3+ regulatory T cells from AB and UCB naïve CD4+ T cells in vitro. (A) FOXP3+ inducible regulatory T cells were generated from AB and UCB naïve CD4+ T cells. FOXP3 expression was measured day 4 induction by FACS analysis (AB, n=9; UCB, n=12). (B) Absolute number of FOXP3+ CD4+ T cells was calculated day 4 iTreg induction. Data are from 4-6 independent experiments. (C) Flow cytometric assay of FOXP3 and CD62L expression on AB (white) and UCB (black) iTregs over 3 weeks in the presence of IL-2. (D) Absolute number of AB (white) and UCB (black) FOXP3+ iTreg cells were calculated at day 14 and 21. Data are from two individual experiments (n=5). * $p<0.05$,  $p<0.01$, ** $p<0.0001$, unpaired Student t test.

TGF-β induced FOXP3 expression was 2.5-fold higher in iTreg derived from UCB CD4+CD45RA+ T cells compared with AB CD4+CD45RA+ T cells (86.8±3.1 vs. 34.3±4.2, n=12; p<0.001) (FIG. 18A). The absolute number of FOXP3+ iTreg generated from UCB vs. AB CD4+CD45RA+ T cells was 4-fold higher ($3.8 \times 10^6$ vs. $1.0 \times 10^6$) (FIG. 18B). Expression of FOXP3 on AB and UCB iTregs quite stable up to 3 weeks but FOXP3 expression was more maintained on UCB iTregs (FIG. 18C). CD62L expression also highly maintained on UCB iTregs (FIG. 18C). Expansion of FOXP3+ iTreg cells was notable for significantly higher absolute numbers of FOXP3+ UCB iTreg compared to AB iTreg (FIG. 18D).

Phenotypic and Functional Characterization of UCB and AB iTreg.

Figures 19A, 19B, 19C:
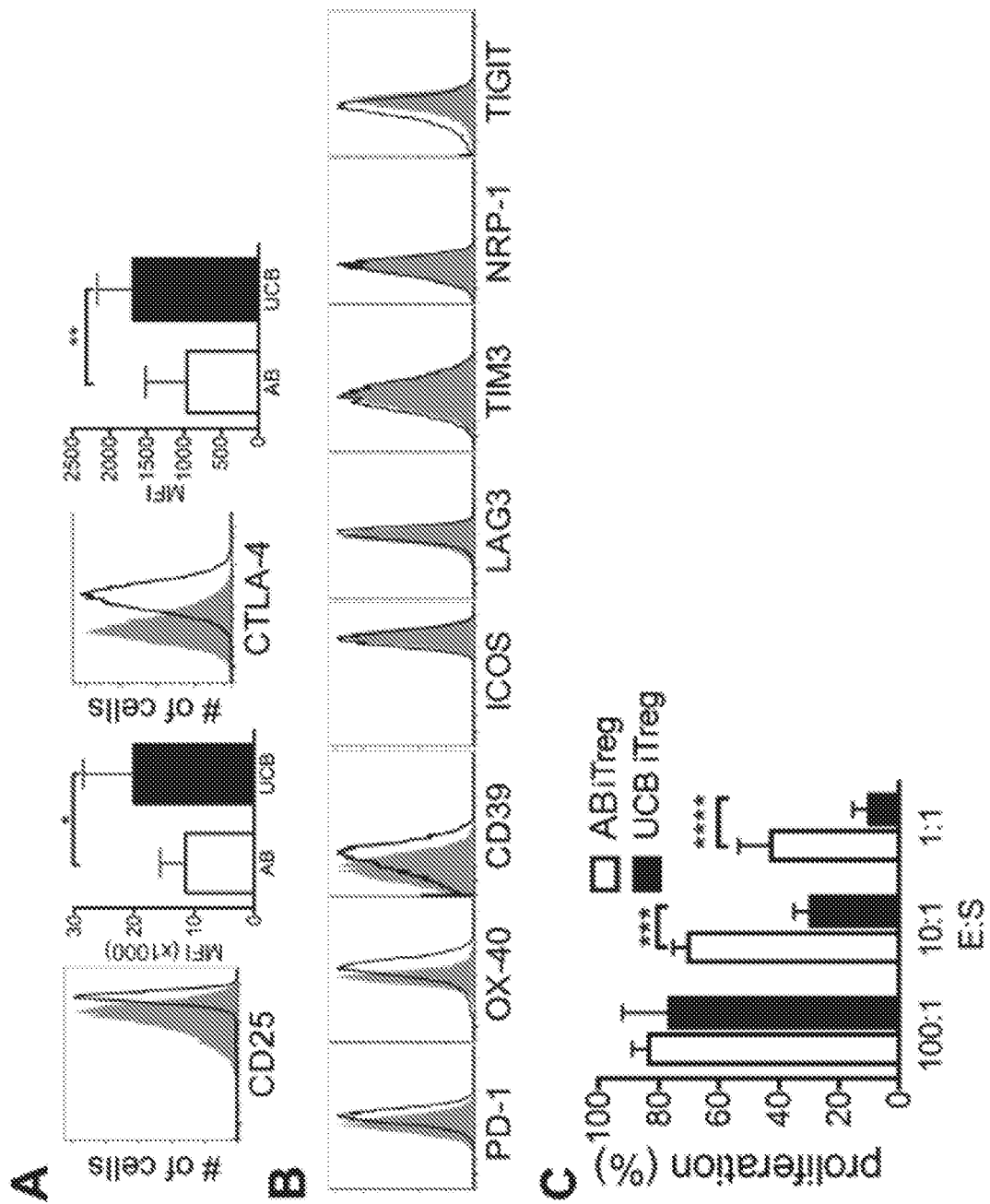
FIGS. 19A-19C show analysis of phenotype and suppressive capacity of AB and UCB FOXP3+ iTreg. (A) FOXP3+ iTreg cells were generated from AB and UCB naïve CD4+ T cells. CD25 and CTLA-4 expression were measured day 4 induction by FACS analysis (AB, n=12; UCB, n=15). (B) Surface expressed inhibitory molecules on FOXP3+ iTreg were analyzed day 4 iTreg induction on AB (solid/filled) and UCB (open) iTregs. (C) Suppression assay of CFSE-labeled AB CD4+ T cells. Suppressive function was assessed according to methods described herein. Data are from two independent experiments (n=4-5). * $p<0.05$,  $p<0.01$, * $p<0.001$, **** $p<0.0001$, unpaired Student t test.

FACS analyses of day 4 iTreg induction revealed that expression of CD25 (AB; 11.4±1.4 vs UCB; 20.1±3.2 MFI) and CTLA-4 (AB; 963.2±167.1 vs UCB; 1691.0±152.2 MFI) were significantly higher on UCB FOXP3+ iTreg compared to AB FOXP3+ iTreg (FIG. 19A). Surface expressed molecules associated with suppressive functions of Treg including OX-40 and CD39 expression were also increased in UCB FOXP3+ iTreg. Expression of PD-1, ICOS, LAGS, TIM-3, NRP-1, and TIGIT were similar or slightly diminished on UCB FOXP3+ iTreg compared to AB (FIG. 19B). AB iTreg demonstrated lower suppressive function compared with UCB iTreg, expressing only ~60% suppression (60.6±6.7) when mixed with responder cells at a 1:1 ratio, and dropping to ~30% suppression (29.9±3.0) at 10:1 ratio (FIG. 19C). By contrast, UCB FOXP3+ iTreg showed enhanced suppressive function with ~90% inhibition (89.9±1.8) at a ratio of 1:1, and ~70% inhibition (70.6±1.9) at a ratio of 10:1 (FIG. 19C). UCB and AB FOXP3+ iTreg suppressive effects were equivalent at a 100:1 ratio.

Knockdown of BACH2 in UCB CD4+Naïve T-Cells Results in Decreased FOXP3 and Downstream CTLA-4 Expression.

Figures 20A, 20B, 20C, 20D:
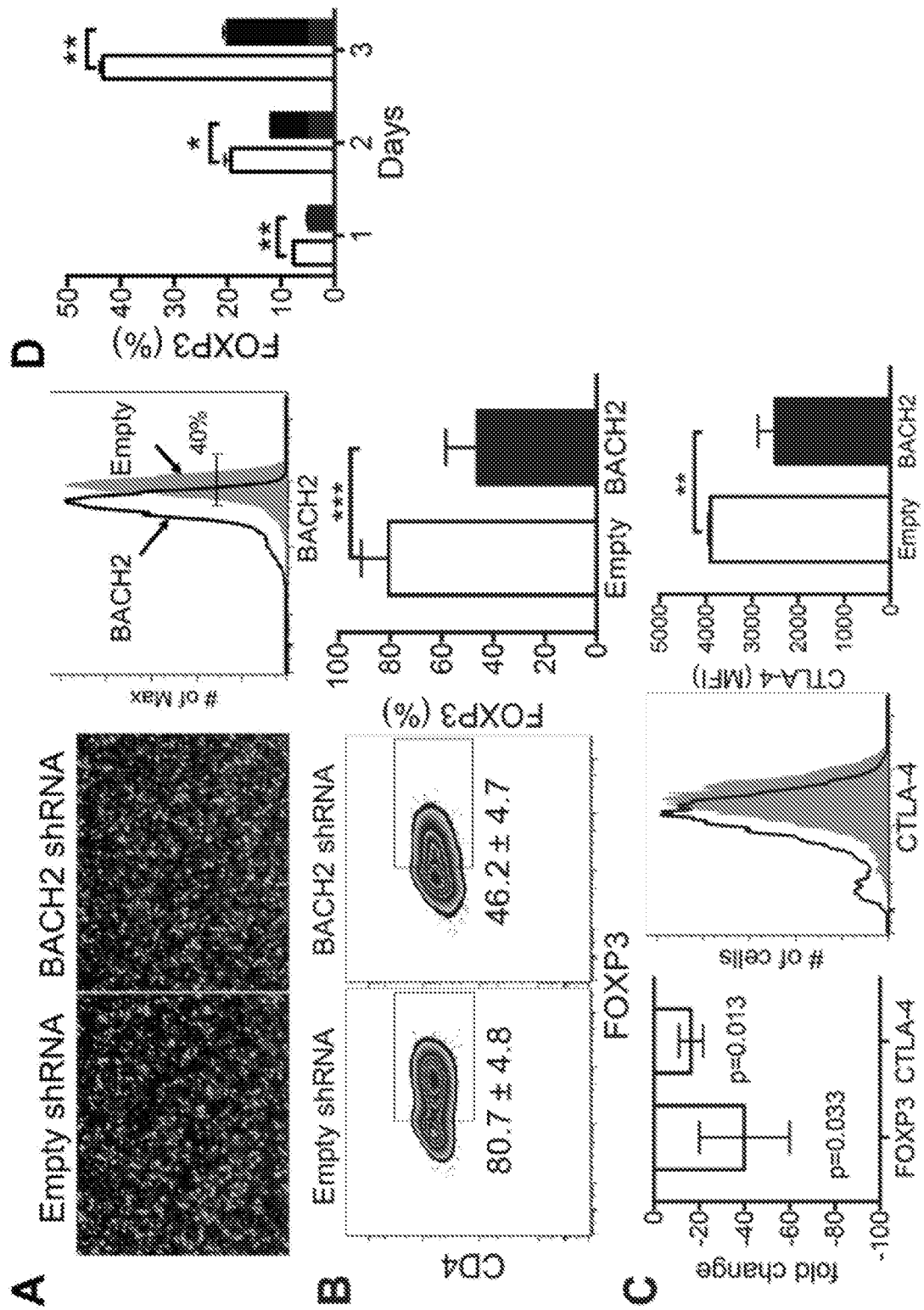
FIGS. 20A-20D show that BACH2 knock down results in reduced FOXP3 and CTLA-4 expression in UCB iTreg. (A) BACH2 expression in Day 4 TGF-β induced UCB iTreg was measured after empty (shaded) and BACH2 (open) shRNA treatment. Data presented are from 3 independent experiments (n=7-8). (B) Expression of FOXP3 in day 4 TGF-β induced UCB iTreg was analyzed after transient transfection with empty and BACH2 shRNA. Data are represented from 3 different experiments (n=7-8). (C) FOXP3 and CTLA-4 mRNA expression in UCB iTreg after Bach2 shRNA treatment was measured by qPCR. CTLA-4 measured by FACS analysis. Data are from two independent experiments (n=4-5) (D) Kinetic measurement of FOXP3 expression in UCB iTreg treated with either empty or BACH2 shRNA transduced UCB naïve CD4+ T cells. Data are from two independent experiments (n=4). * $p<0.05$,  $p<0.01$, * $p<0.001$, unpaired Student t test.

To address the potential role for BACH2 transcriptional regulation in UCB naïve CD4+ T cells, BACH2 shRNA knockdown was performed as described above (FIG. 20A). CD4 iTreg were lentiviral transfected with GFP tagged empty or BACH2 shRNA virus. BACH2 shRNA transduction reduced BACH2 expression on UCB CD4+ T cells compared to empty shRNA. FOXP3 expression in UCB CD4+ T cells transiently transfected with BACH2 shRNA results in approximately 40% reduction (empty; 80.7±3.7% vs BACH2; 46.2±4.6%) in the number of cells differentiated into FOXP3+ iTreg (FIG. 20B). As a consequence of BACH2 shRNA knockdown, levels of CTLA-4 mRNA and protein expression in transiently transfected UCB CD4+ T cells dropped to a 12-fold lower mRNA and a 2-fold lower protein expression (FIG. 20C). FOXP3 expression after BACH2 shRNA transduction in UCB naïve CD4+ T cells was also measured by time kinetics. As shown in FIG. 20D, FOXP3 expression progressively increased in empty vector shRNA transduced UCB CD4+ T cells compared to BACH2 shRNA transduced UCB CD4+ T cells.

Identification of Putative Transcriptional BACH2 Binding Sites.

Based on the results of BACH2 shRNA knockdown in naïve CD4+ T-cells, further studies were conducted to determine whether BACH2 could potentially bind to the proximal region of exon −1 promoter region of the human FOXP3 gene. BACH2, AP-1, and NFAT1 consensus DNA binding sequences were compared with the promoter region of human FOXP3.[30] Sequence analysis of the human FOXP3 promoter region confirmed the known AP-1 binding sites which were >75% similar to the BACH2 consensus binding sites (FIG. 21A). The proximal region of FOXP3-1 exon region contained putative NFAT1 binding sites as well (FIG. 21A). Overall, this analysis identifies sequences with BACH2 consensus DNA binding sites identified within the promoter region of human FOXP3.

Cross-Linking Chromatin-Immunoprecipitation Assay (ChIP Assay).

Based on observed higher expression of BACH2 in UCB naïve CD4+ T-cells vs. AB and higher FOXP3 expression in day 4 UCB iTreg, further studies were conducted to determine whether BACH2 binds to the FOXP3 promoter in CD4+ iTreg. AB and UCB naïve CD4+ T cells were differentiated into iTreg as described above. Cells were collected day 4 (96 h stimulation) and processed for ChIP assays. As shown in FIG. 21B, binding of BACH2 to the FOXP3 promoter region was significantly higher in UCB FOXP3+ iTregs vs. AB. These results were confirmed using standard gel electrophoresis (FIG. 21C).

Luciferase Assay at the FOXP3 Promoter Region.

Figure 22:
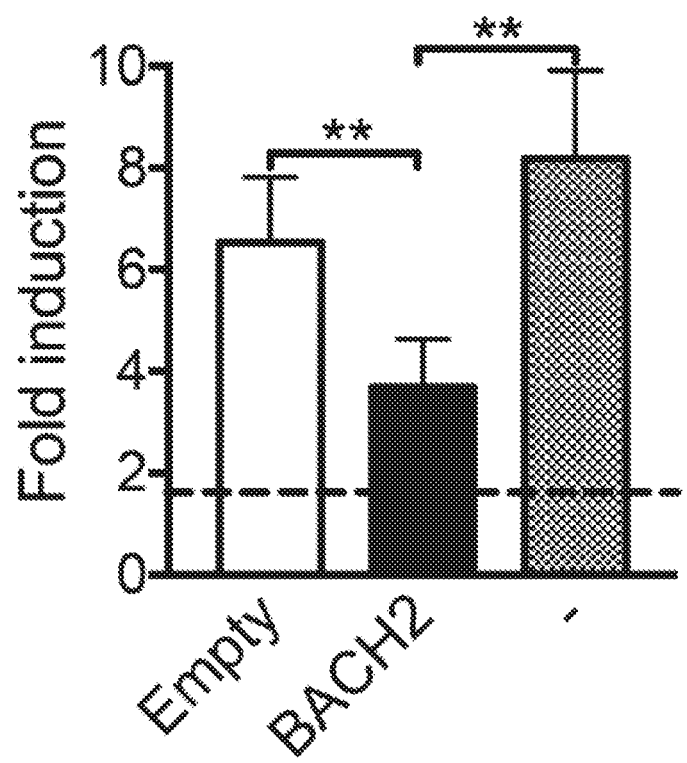
FIG. 22 shows that BACH2 molecule is transcriptionally active at the FOXP3 promoter. FOXP3 reporter (Luc) Jurkat recombinant cells were stimulated with CD2/3/28 dyna-beads. FOXP3 promoter activity measured by luciferase assay after empty or BACH2 shRNA treatment of human FOXP3 reporter. Fold induction of luminescence was calculated based on media condition (dotted line). Data are from 10 individually tested samples. ** p<0.01, unpaired Student t test.

To confirm whether BACH2 is transcriptionally active at the FOXP3 promoter, luciferase activity was measured in FOXP3 luciferase reporter cells transiently transfected with either empty or BACH2 shRNA. TCR stimulation increased luciferase expression. Empty shRNA treatment did not affect luciferase expression (FIG. 22). However, BACH2 shRNA treatment significantly diminished luciferase expression compared to empty shRNA treated cells (FIG. 22).

Figures 23A, 23B:
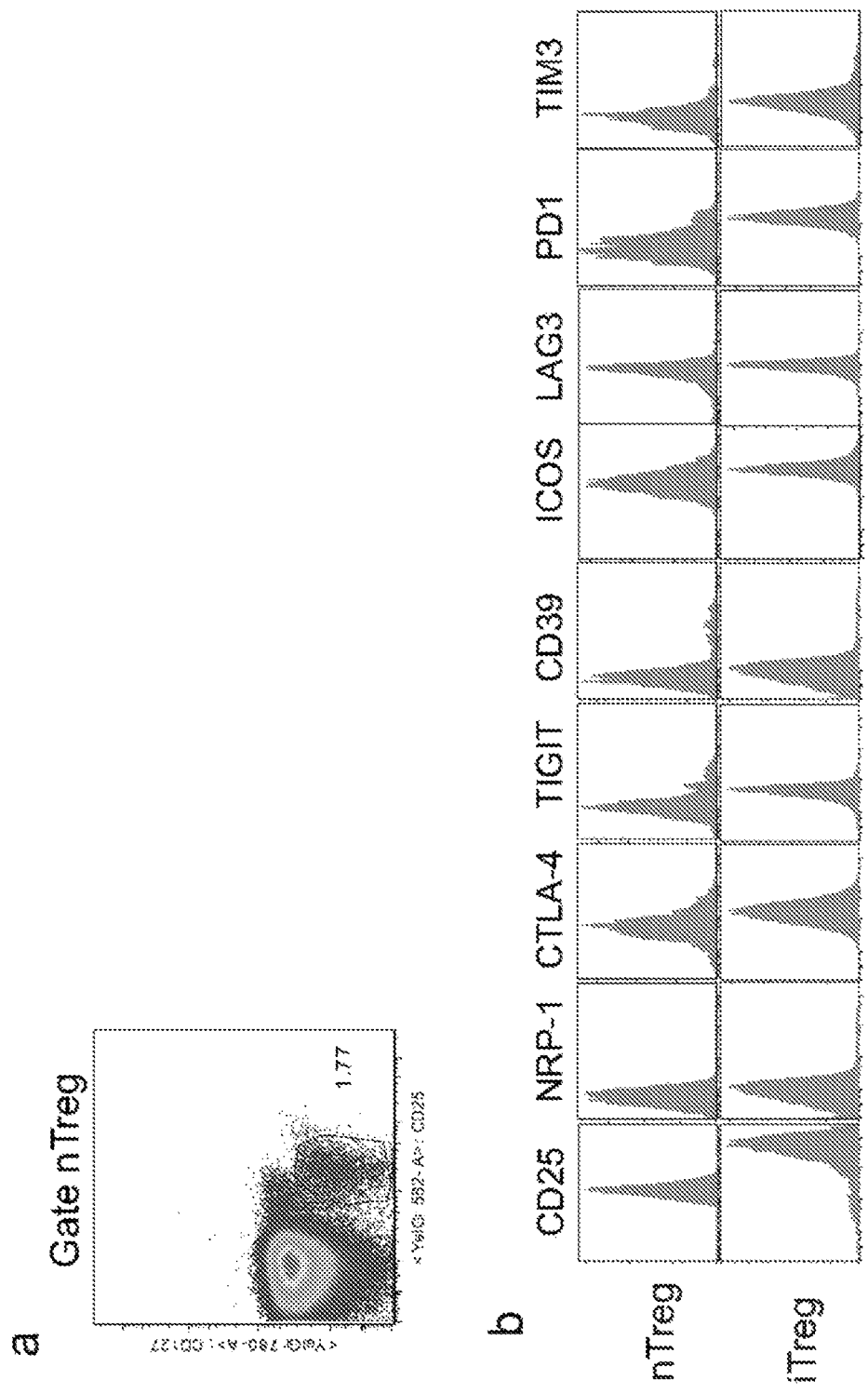

FIGS. 23A-23-B show Comparison of inhibitory molecules expression on UCB CD4+CD127lowCD25+ natural Treg and iTreg cells. (A) Gating note for nTreg sort from UCB. (B) Surface and cytoplasmic (CTLA-4) staining in nTreg and iTreg. 1-5×105 cells were stained with each antibody. Expression was measured by FACS analysis (n=3-5).

Figure 24:
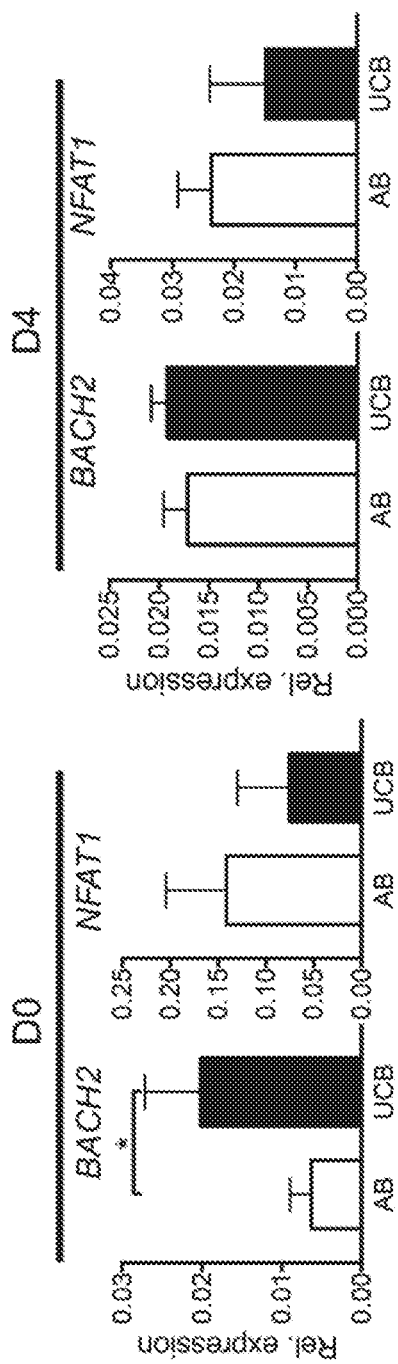
FIG. 24 shows analysis of BACH2 and NFAT1 RNA expression by qRT-PCR in AB and UCB naive CD4 at baseline day 0 (D0) and Day 4 after differentiation with CD2/3/28-stimulation, IL-2 100 U/ml, and TGF-β 5 ng/ml. Data are presented as relative mRNA expression (n=3-8).
Figures 25A, 25B, 25C, 25D:
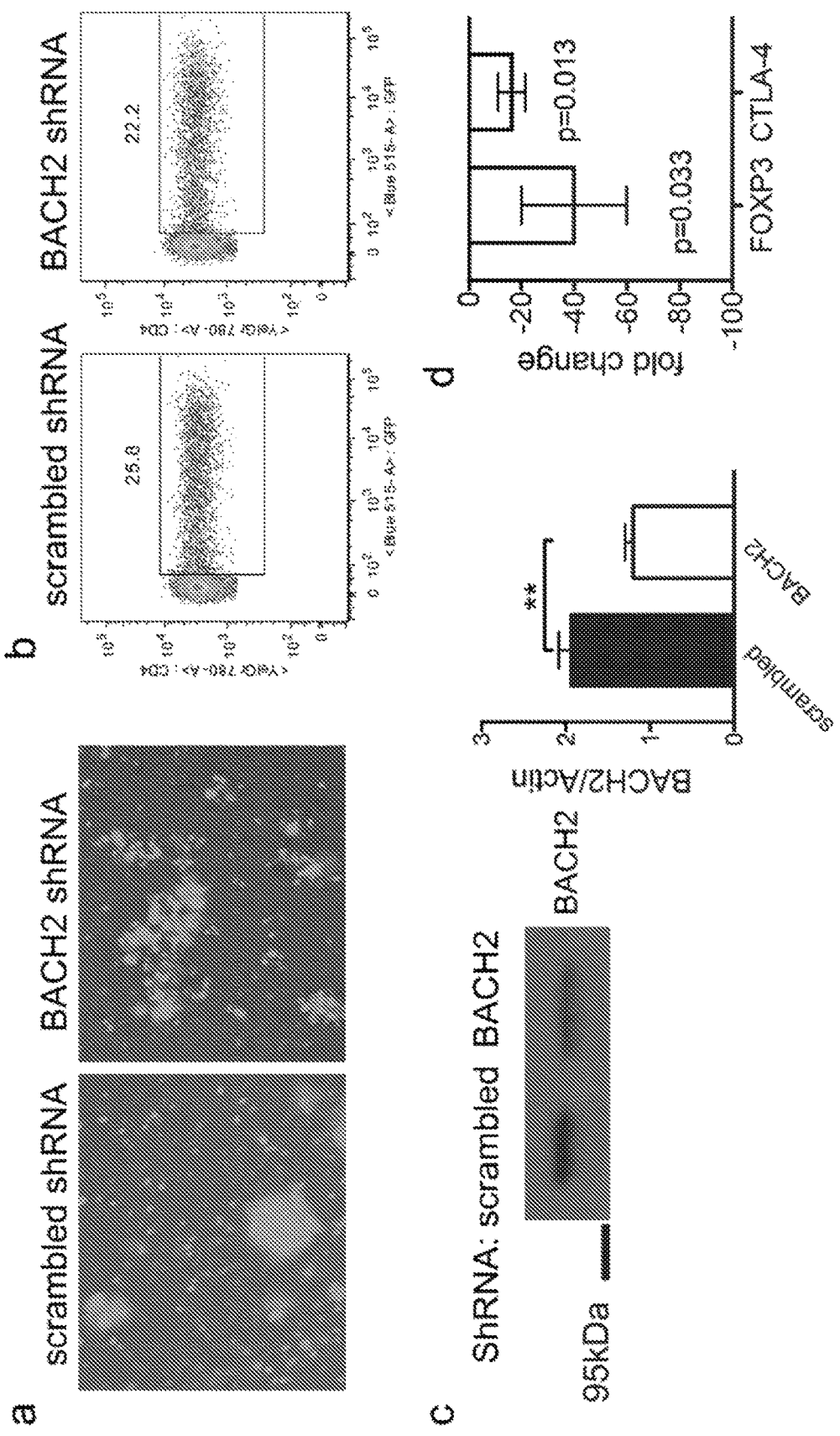
FIGS. 25A-25D show transduction efficient of UCB naïve CD4 T cells using GFP lentivirus. (A) Transduction of UCB naïve CD4 T cells with GFP lentivirus. Fluorescence of naive CD4 T cells was measured 72 hr after transduction. (B) Gating strategy for the GFP lentivirus transduced CD4 T cells FACS purification. Doublets was excluded by FSH-A and FSH-H plot. (C) Analysis of BACH2 protein expression by western blot from lenti viral transduced CD4 T cells. (D) Foxp3 and CTLA-4 mRNA expression in GFP+ UCB iTreg after BACH2 shRNA treatment was measured by qPCR. Data are from two independent experiments (n=4-5).

FIG. 24 shows analysis of BACH2 and NFAT1 RNA expression by qRT-PCR in AB and UCB naive CD4 at baseline day 0 (D0) and Day 4 after differentiation with CD2/3/28-stimulation, IL-2 100 U/ml, and TGF-β 5 ng/ml. Data are presented as relative mRNA expression (n=3-8).

FIGS. 25A-25D show transduction efficient of UCB naïve CD4 T cells using GFP lentivirus. (A) Transduction of UCB naïve CD4 T cells with GFP lentivirus. Fluorescence of naive CD4 T cells was measured 72 hr after transduction. (B) Gating strategy for the GFP lentivirus transduced CD4 T cells FACS purification. Doublets was excluded by FSH-A and FSH-H plot. (C) Analysis of BACH2 protein expression by western blot from lenti viral transduced CD4 T cells. (D) Foxp3 and CTLA-4 mRNA expression in GFP+ UCB iTreg after BACH2 shRNA treatment was measured by qPCR. Data are from two independent experiments (n=4-5).

Figure 26A:
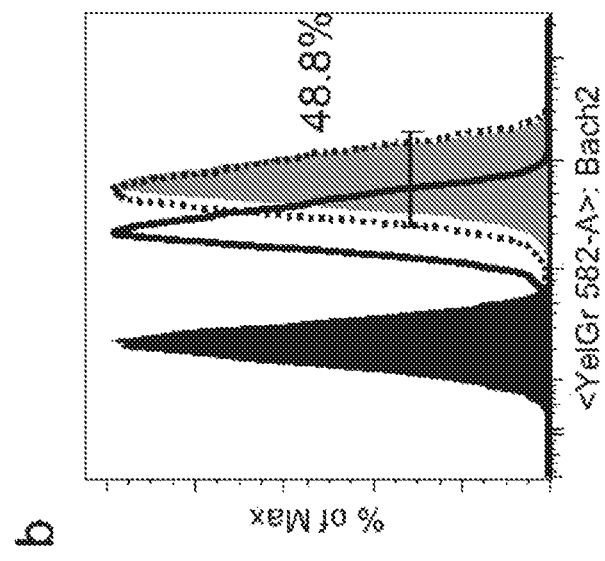
FIG. 26A-26B show quantification analysis of BACH2 protein on Foxp3 reporter Jurkat cells. (A) BACH2 expression was measured by western blot in Foxp3 reporter Jurkat cells. 5×10$^5$ cells were stimulated with 5 ng/ml TGF-β. Whole cell lysates collected at indicated time. (B) FACS analysis for BACH2 expression. Cells were collected and stained with BACH2 Ab followed PE-anti-rat IgG (H+L) secondary Ab. No primary Ab (black sold), TCR stimulation (gray sold), scrambled shRNA treated (dot line) and BACH2 shRNA treated (black line).
Figure 26B:
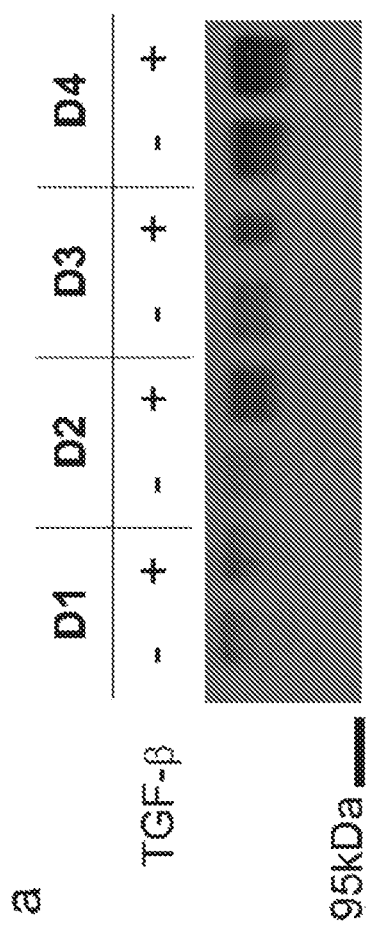

FIG. 26A-26B show quantification analysis of BACH2 protein on Foxp3 reporter Jurkat cells. (A) BACH2 expression was measured by western blot in Foxp3 reporter Jurkat cells. 5×10⁵ cells were stimulated with 5 ng/ml TGF-β. Whole cell lysates collected at indicated time. (B) FACS analysis for BACH2 expression. Cells were collected and stained with BACH2 Ab followed PE-anti-rat IgG (H+L) secondary Ab. No primary Ab (black sold), TCR stimulation (gray sold), scrambled shRNA treated (dot line) and BACH2 shRNA treated (black line).

The findings, based on comparative FACS analyses, assessment of iTreg suppressive function, chromatin immunoprecipitation, shRNA knock down, and luciferase measurements, demonstrate that BACH2 regulates in vitro TGF-β induced FOXP3 expression in iTreg differentiated from UCB naïve CD4⁺45RA⁺ T-cells. Increased BACH2 expression in UCB naïve CD4⁺45RA⁺ T-cells may serve as a strong promoter of FOXP3 expression in TGF-β induced FOXP3⁺ iTreg that was observed to be sustained during 21 day in vitro expansion. During TGF-β induced FOXP3⁺ iTreg generation, it was noted that low levels of BACH2 in AB naïve CD4⁺45RA⁺ T-cells are insufficient to upregulate FOXP3 and stably sustain its expression during attempted 21 day iTreg expansion in vitro. As sustained FOXP3 expression is required for Treg lineage maintenance and suppressive function, instability of FOXP3 in iTreg compared with nTreg has to date severely limited the clinical development of iTreg for GVHD prophylaxis. It has been demonstrated that instability of FOXP3 expression in iTreg limits the utility of adoptively transferred iTreg as a source of cellular therapy for the abrogation of GVHD. However, the low frequency of nTreg in human peripheral blood provides strong rationale to generate and expand large numbers of stable FOXP3-expressing iTreg for adoptive therapy as GVHD prophylaxis, as high numbers of Treg are needed for effective immunotherapy in humans to facilitate tolerance after allogeneic stem cell transplantation. This disclosure provides methods that are able to generate 1-4× 10⁹ iTreg with a 21 day expansion protocol from each individual UCB unit, which meets the needs of human clinical application, with however noted variance in iTreg cell yield between different UCB units.

TGF-β induced FOXP3⁺ UCB iTreg were observed to have enhanced suppressive function vs. AB iTreg. Significantly upregulated expression of two well described inhibitory molecules expressed by Treg, e.g. CD25 and CTLA-4, was also observed on UCB FOXP3⁺ iTreg. Expression of other surface inhibitory and exhaustion molecules including PD-1, ICOS, LAG-3, TIM-3, NRP-1, and TIGIT did not differ between AB and UCB FOXP3⁺ iTreg. However, enhanced expression of OX-40 and CD39 on UCB iTreg was observed, which may also contribute to the enhanced suppressive function of UCB iTreg. Significantly higher CD62L surface expression, the receptor that is required for entry into lymph nodes, was observed and was sustained on UCB iTreg during 21 day in vitro expansion.

FOXP3 associates with a large number of co-factors and is modified by histone acetylation, thereby maintaining Treg lineage and suppressive function. The present findings revealed significant loss of FOXP3 expression in BACH2 shRNA transfected UCB naïve CD4⁺ T-cells. Expression levels of CTLA-4 were examined in BACH2 shRNA transfected UCB CD4⁺ T-cells to determine further the effects of FOXP3 reduced expression in stimulated UCB CD4⁺ T-cells. The data showed significant loss of CTLA-4 expression under conditions of reduced FOXP3 expression. These findings support the concept that CTLA-4 is associated with Treg transcriptional signature.

Provided herein is a mechanism for FOXP3 gene activation including important transcription factors for development of CD4⁺25⁺ Treg. Since the FOXP3 promoter is activated by IL-2 through STAT5, UCB CD4⁺45RA⁺ T-cells may be primed for expression of the FOXP3 gene, as it has been shown that STAT5 binds de-acetylated histone 4 for trans-activation. UCB CD4⁺45RA⁺ T-cells have reduced NFAT1 protein expression, and hypo-acetylated histone 3 and 4 at the FOXP3 promoter, which indicates that primary stimulation and IL-2 expansion conditions (i.e., CD3 and CD28 co-stimulation) plus high dose IL-2 results in a muted Th1 response and sustained FOXP3 gene expression.

In aspects, the present disclosure identifies an important difference in molecular mechanisms of iTreg generation and maintenance between naïve CD4⁺ T cells from normal adults and neonates with implications for autoimmunity and tolerance. In aspects, the present disclosure identifies BACH2 an important transcription factor that interacts with and regulates FOXP3 that governs iTreg vs. effector T cell differentiation and function. BACH2 robust expression in UCB CD4⁺ T cells may be considered one mechanism underlying the altered response of UCB CD4⁺ T cells in ex vivo iTreg expansion culture compared with AB CD4⁺ T cells. BACH2 regulation in human UCB iTreg is exerted via direct transcriptional activity at the FOXP3 promoter.

The differing BACH2 regulation between UCB and AB naïve CD4 T cells has important implications for molecular mechanisms underlying neonatal tolerance and normal human T-cell repertoire development. The neonatal period of immune tolerance allows for adaptive immunity development, distinguishing self-antigens from non-self, a process that may be important to the prevention of autoimmunity. BACH2 plays an important role in the differentiation, maintenance, and function of UCB iTreg, and the effect of BACH2 in UCB naïve CD4 T-cell differentiation may support the clinical development and use of UCB iTreg for adoptive cellular therapy for GVHD prophylaxis.

In sum, FOXP3 is important for T-regulatory (Treg) induction and function, and can stabilize Treg immune homeostasis. The present disclosure identifies BACH2 as playing an important role in FOXP3 regulation, namely BACH2 serves to stabilize robust FOXP3 expression in human UCB CD4 T cell-derived iTreg. FOXP3 expression and regulation was examined by comparing human induced Treg (iTreg) differentiated from UCB and adult blood (AB) naïve CD4 T-cells. FOXP3 expression was 2.5-fold higher in UCB-derived iTreg vs. AB and was sustained during 21 day iTreg in vitro expansion. The absolute number of FOXP3+ iTreg generated from UCB vs. AB naive CD4+ T cells was 4-fold higher in iTreg TGFβ differentiation conditions. In addition, suppressive function of UCB iTreg was more potent in mixed lymphocyte culture compared to AB iTreg. Naïve UCB CD4+ T cells highly expressed BACH2, with 21-fold higher mRNA and 5-fold higher protein expression compared to AB CD4⁺ T cells. Putative transcriptional BACH2 binding sites were identified at the FOXP3 promoter using BACH2 consensus sequence. Cross-linking chromatin immunoprecipitation (ChIP) showed that BACH2 binds to the human FOXP3 proximal promoter in UCB iTreg, but not AB iTreg. BACH2 was noted to be transcriptionally active with decreased FOXP3 gene transcription by luciferase in UCB CD4+ T-cells transfected with BACH2 shRNA. BACH2 transient shRNA knockdown resulted in 36-fold reduction of FOXP3 as well as 16-fold reduction of CTLA-4 mRNA and 2-fold reduction in protein expression. Taken together, the present disclosure provides that (1) UCB naïve CD4 T cell-derived iTreg exhibit robust and sustained FOXP3 expression during 21 day expansion, and (2)

BACH2 serves to stabilize FOXP3 expression in human UCB naïve CD4 T cell derived iTreg.

The present disclosure's methods for producing inducible regulatory T cells from umbilical cord blood may yield UCB-derived iTregs having a higher expression of BACH2, which may contribute to the immune tolerance of UCB graft T-cells vs. adult donor mobilized peripheral blood and bone marrow grafts, allowing successful allogeneic transplantation despite ≥2 loci HLA disparity, without requirement of T depletion, with noted lower GVHD incidence and severity, and maintained graft vs. malignancy effects.

The invention claimed is:

1. An inducible regulatory T cell composition comprising an expanded iTreg composition produced by a method comprising:
    providing human umbilical cord blood;
    isolating naïve CD4$^+$ T cells from the human umbilical cord blood;
    inducing the naïve CD4$^+$ T cells to differentiate into a first composition comprising iTregs by treating the naïve CD4$^+$ T cells with TGF-β;
    separating the iTregs from the first composition to form a substantially purified iTreg composition; and
    expanding the purified iTreg composition in a composition comprising a mesenchymal stromal cell (MSC) feeder layer and IL-2 to form an expanded human iTreg composition expressing CD4$^+$, CD25$^+$, CD45RA$^+$ and Foxp3$^+$ proteins at higher levels than iTregs not expanded over a MSC feeder cell layer.

2. A therapeutic regulatory T cell composition comprising a therapeutically effective dose of human umbilical cord blood derived iTregs expanded in a composition comprising mesenchymal stromal cells and IL-2.

3. A therapeutic composition comprising a therapeutic T cell composition made by a method comprising:
    providing human umbilical cord blood;
    isolating naïve CD4$^+$ T cells from the umbilical cord blood; and
    manufacturing a therapeutic T cell composition comprising iTregs from the isolated naïve CD4$^+$ T cells, wherein the manufacturing comprises expanding the iTregs in a composition comprising a mesenchymal stromal cell (MSC) feeder layer and IL-2.

4. The inducible regulatory T cell composition of claim 1, wherein the iTregs are separated from the first composition using flow cytometry cell sorting or magnetic cell sorting.

5. The inducible regulatory T cell composition of claim 1, wherein the purified iTreg composition is at least 90% pure.

6. The therapeutic regulatory T cell composition of claim 2, wherein the expanded human iTregs express CD4+, CD25+, CD45RA+ and Foxp3+ proteins at higher levels than iTregs not expanded over a MSC feeder layer.

7. The therapeutic composition of claim 3, wherein the T cell composition comprises expanded human iTregs expressing CD4+, CD25+, CD45RA+ and Foxp3+ proteins at higher levels than iTregs not expanded over a MSC feeder layer.

8. The inducible regulatory T cell composition of claim 1, wherein the expanded human iTreg composition expresses CTLA4, CD25, and Foxp3 at higher levels compared to iTregs prepared from CD4$^+$ T cells derived from adult blood.

9. The inducible regulatory T cell composition of claim 1, wherein the expanded human iTreg composition has an enhanced ability to modulate dendritic cells compared to iTregs prepared from CD4$^+$ T cells derived from adult blood.

10. The inducible regulatory T cell composition of claim 1, wherein the expanded human iTreg composition has an enhanced stability of Foxp3 expression compared to iTregs prepared from CD4$^+$ T cells derived from adult blood.

11. The inducible regulatory T cell composition of claim 1, wherein the expanded human iTreg composition has an enhanced suppressive activity compared to iTregs prepared from CD4$^+$ T cells derived from adult blood.

12. The therapeutic regulatory T cell composition of claim 1, wherein the human umbilical cord blood derived iTregs express CTLA4, CD25, and Foxp3 at higher levels compared to adult blood derived iTregs.

13. The therapeutic regulatory T cell composition of claim 1, wherein the human umbilical cord blood derived iTregs have an enhanced stability of Foxp3 expression compared to iTregs prepared from CD4$^+$ T cells derived from adult blood.

14. The therapeutic composition of claim 3, wherein the iTregs manufactured from the naïve CD4$^+$ T cells isolated from the umbilical cord blood express CTLA4, CD25, and Foxp3 at higher levels compared to iTregs manufactured from naïve CD4$^+$ T cells isolated from adult blood.

15. The therapeutic composition of claim 3, wherein the iTregs manufactured from the naïve CD4$^+$ T cells isolated from the umbilical cord blood have an enhanced stability of Foxp3 expression compared to iTregs manufactured from naïve CD4$^+$ T cells isolated from adult blood.

16. The inducible regulatory T cell composition of claim 1, wherein the inducing and expanding steps are performed without rapamycin.

17. The inducible regulatory T cell composition of claim 1, wherein the MSC feeder layer is derived from a healthy subject.

* * * * *